(12) United States Patent
Cho et al.

(10) Patent No.: US 10,145,785 B2
(45) Date of Patent: Dec. 4, 2018

(54) OPTICAL ELEMENT ROTATION TYPE MUELLER-MATRIX ELLIPSOMETER AND METHOD FOR MEASURING MUELLER-MATRIX OF SAMPLE USING THE SAME

(71) Applicant: KOREA RESEARCH INSTITUTE OF STANDARDS AND SCIENCE, Daejeon (KR)

(72) Inventors: Yong Jai Cho, Daejeon (KR); Won Chegal, Daejeon (KR); Hyun Mo Cho, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 295 days.

(21) Appl. No.: 14/906,433

(22) PCT Filed: May 13, 2014

(86) PCT No.: PCT/KR2014/004267
§ 371 (c)(1),
(2) Date: Jan. 20, 2016

(87) PCT Pub. No.: WO2015/030343
PCT Pub. Date: Mar. 5, 2015

(65) Prior Publication Data
US 2016/0153894 A1 Jun. 2, 2016

(30) Foreign Application Priority Data
Aug. 30, 2013 (KR) ........................ 10-2013-0103738

(51) Int. Cl.
*G01N 21/21* (2006.01)
*G01J 4/00* (2006.01)
*G01J 4/04* (2006.01)

(52) U.S. Cl.
CPC .............. *G01N 21/211* (2013.01); *G01J 4/00* (2013.01); *G01J 4/04* (2013.01); *G01J 2004/001* (2013.01);
(Continued)

(58) Field of Classification Search
CPC ........ G01J 4/00; G01J 4/02; G01J 4/04; G01J 2004/001; G01J 2004/002;
(Continued)

(56) References Cited

U.S. PATENT DOCUMENTS 4,306,809 A 12/1981 Azzam
7,224,471 B2 5/2007 Bischoff et al.
(Continued)

FOREIGN PATENT DOCUMENTS

KR 1020100064612 A 6/2010
KR 1020110035811 A 4/2011
KR 1020130019495 A 2/2013

OTHER PUBLICATIONS

Aspnes, D. et al., "Rotating-Compensator/Analyzer Fixed-Analyzer Ellipsometer: Analysis and Comparison to Other Automatic Ellipsometers," Journal of the Optical Society of America, vol. 66, No. 9, Sep. 1976, 6 pages.
(Continued)

*Primary Examiner* — Gordon J Stock, Jr.
(74) *Attorney, Agent, or Firm* — McCoy Russell LLP

(57) ABSTRACT

Provided is an optical element rotation type Mueller-matrix ellipsometer for solving a problem of measurement accuracy and measurement precision occurring due to residual polarization of a light source, polarization dependence of a photo-detector, measurement values of Fourier coefficients of a high order term in dual optical element rotation type Mueller-matrix ellipsometers according to the related art
(Continued)

capable of measuring some or all of components of a Mueller-matrix for any sample.

12 Claims, 10 Drawing Sheets

(52) U.S. Cl.
CPC .................. *G01N 2021/213* (2013.01); *G01N 2201/0683* (2013.01); *G01N 2201/11* (2013.01)

(58) Field of Classification Search
CPC ........... G01J 2004/004; G01J 2004/005; G01J 2004/007; G01J 2004/008; G01N 2201/061; G01N 2201/0633; G01N 2201/0683; G01N 2201/11; G01N 21/211; G01N 2021/213; G01N 2021/214; G01N 2021/215
See application file for complete search history.

(56) References Cited

U.S. PATENT DOCUMENTS

| | | | |
|---|---|---|---|
| 7,277,172 B2 | 10/2007 | Kandel et al. | |
| 7,414,733 B2 | 8/2008 | Bischoff et al. | |
| 7,990,549 B2 | 8/2011 | Walsh | |
| 8,446,584 B2 | 5/2013 | Krishnan et al. | |
| 8,447,546 B2 * | 5/2013 | Cho | G01J 1/42 702/66 |
| 8,830,463 B2 * | 9/2014 | Cho | G01N 21/211 356/369 |
| 9,581,498 B2 * | 2/2017 | Cho | G01J 3/447 |
| 2007/0229826 A1 | 10/2007 | Schubert | |
| 2010/0328640 A1 * | 12/2010 | Uemura | G01J 4/00 355/71 |
| 2011/0080585 A1 | 4/2011 | Rabello et al. | |

OTHER PUBLICATIONS

Azzam, R., "Photopolarimeter Using Two Modulated Optical Rotators," Optics Letters, vol. 1, No. 5, Nov. 1977, 3 pages.
Azzam, R., "Photopolarimetric Measurement of the Mueller Matrix by Fourier Analysis of a Single Detected Signal," Optics Letters, vol. 2, No. 6, Jun. 1978, 3 pages.
Hauge, P., "Recent Developments in Instrumentation in Ellipsometry," Surface Science, vol. 96, No. 1-3, Jun. 1980, 33 pages.
Chen, C. et al., "Multichannel Mueller Matrix Ellipsometer Based on the Dual Rotating Compensator Principle," Thin Solid Films, vol. 455-456, May 1, 2004, 10 pages.
ISA Korean Intellectual Property Office, International Search Report Issued in Application No. PCT/KR2014/004267, dated Jul. 31, 2014, WIPO, 2 pages.

* cited by examiner

OPTICAL ELEMENT ROTATION TYPE MUELLER-MATRIX ELLIPSOMETER AND METHOD FOR MEASURING MUELLER-MATRIX OF SAMPLE USING THE SAME

The present application is a U.S. National Phase of International Patent Application Serial No. PCT/KR2014/004267, entitled "OPTICAL ELEMENT ROTATION TYPE MUELLER-MATRIX ELLIPSOMETER AND METHOD FOR MEASURING MUELLER-MATRIX OF SAMPLE USING THE SAME," filed on May 13, 2014, which claims priority to Korean Patent Application No. 10-2013-0103738, entitled "OPTICAL ELEMENT ROTATION TYPE MUELLER-MATRIX ELLIPSOMETER AND METHOD FOR MEASURING MUELLER-MATRIX OF SAMPLE USING THE SAME," filed on Aug. 30, 2013.

TECHNICAL FIELD

The present invention relates to an optical element rotation type ellipsometer, and more particularly, to an ellipsometer used to measure Mueller-matrix components of a sample by measuring and analyzing a change in a polarization state of light reflected or transmitted by the sample.

BACKGROUND ART

In industrial fields associated with a semiconductor device, a flat panel display, a nano-bio, a nano-imprint, thin film optics, and the like, that have been rapidly developed, importance of a technology capable of non-destructively and contactlessly measuring and evaluating physical properties such as a thicknesses of a thin film of nano samples, a shape of a nano pattern, and the like, in a manufacturing process step has gradually increased.

In accordance with the continuously development of these industrial fields, the thickness of the thin film has been gradually decreased to arrive at a level of several atom layers, and the shape of the nano pattern has become complicated from an existing two-dimensional structure to a three-dimensional structure.

Therefore, in an ellipsometric technology field used as a measuring equipment for a process in these industrial fields, a Mueller-matrix ellipsometer has been developed and used in order to more accurately measure the complicated shape or the complicated physical feature of the sample as described above.

The most widely used Mueller-matrix ellipsometer among Mueller-matrix ellipsometers according to a first exemplary embodiment is an optical element rotation type Mueller-matrix ellipsometer as shown in FIG. 1. The optical element rotation type Mueller-matrix ellipsometer as shown in FIG. 1 is well known as a nano measuring apparatus in which incident light 10 is parallel light generated from a light source 11, and is modified into a specific polarization state by a polarization modifying unit 12 and is then irradiated to a sample 20 to become reflected light (or transmitted light) 30 of which a polarization state is changed by reflection (or transmission) by the sample 20, the change in the polarization state of the reflected light (or the transmitted light) 30 by the sample is measured with respect to any wavelength and incident angle using a polarization analyzing unit 31 and a photo-detector 32, and the measured data are analyzed to find physical property and shape information of the sample.

A core configuration of the optical element rotation type Mueller-matrix ellipsometer will be described. The light source 11, and the polarization modifying unit 12, which is an optical system allowing the light emitted from the light source 11 to be in a specific polarization state, are disposed on a line of the incident light 10, and the polarization analyzing unit 31, which is an optical system analyzing the polarization state of the reflected light (or the transmitted light) and the photo-detector 32 measuring an amount of light passing through the polarization analyzing unit 31 as an electrical signal such as a voltage or a current are disposed on a line of the reflected light (or the transmitted light) 30.

The most widely used Mueller-matrix ellipsometer among various kinds of Mueller-matrix ellipsometers according to the related art is a dual optical element rotation type ellipsometer in which two optical elements rotate at a constant velocity in a predetermined speed ratio. A typical example of the dual optical element rotation type ellipsometer includes a rotating-polarizer rotating-analyzer ellipsometer as shown in FIG. 2, a rotating-compensator rotating-analyzer ellipsometer as shown in FIG. 3, a rotating-polarizer rotating-compensator ellipsometer as shown in FIG. 4, and a dual-rotating-compensator ellipsometer as shown in FIG. 5.

A core component of the rotating-polarizer rotating-analyzer ellipsometer according to a second exemplary embodiment is that the polarization modifying unit 12 is configured of a linear polarizer (commonly called a polarizer 13) rotating at a constant velocity and the polarization analyzing unit 31 is configured of a linear polarizer (commonly called analyzer 33) rotating at a constant velocity in a predetermined ratio different from that of the polarizer 13, as shown in FIG. 2.

A core component of the rotating-compensator rotating-analyzer ellipsometer according to a third exemplary embodiment is that the polarization modifying unit 12 is configured of the polarizer 13 stopping at a designated azimuth angle and a first compensator 14 rotating at a constant velocity and the polarization analyzing unit 31 is configured of an analyzer 33 rotating at a constant velocity in a predetermined ratio different from that of the first compensator 14, as shown in FIG. 3.

A core component of the rotating-polarizer rotating-compensator ellipsometer according to a fourth exemplary embodiment is that the polarization modifying unit 12 is configured of the polarizer 13 rotating at a constant velocity and the polarization analyzing unit 31 is configured of a second compensator 34 rotating at a constant velocity in a predetermined ratio different from that of the polarizer 13 and the analyzer 33 stopping at a designated azimuth angle, as shown in FIG. 4.

A core component of the dual-rotating-compensator ellipsometer according to a fifth exemplary embodiment is that the polarization modifying unit 12 is configured of the polarizer 13 stopping at a designated azimuth angle and the first compensator 14 rotating at a constant velocity and the polarization analyzing unit 31 is configured of the second compensator 34 rotating at a constant velocity in a predetermined ratio different from that of the first compensator 14 and the analyzer 33 stopping at a designated azimuth angle, as shown in FIG. 5.

In these dual optical element rotation type ellipsometer, a Fourier coefficient analyzing method is used in order to analyze a waveform of light intensity when the light intensity periodically changed depending on a time t by rotation of optical elements is measured using a photo-detector in real time.

In the case in which it is assumed that an error is not present in this measuring apparatus, light intensity $I_{ex}(t)$ measured as an electrical signal such as a voltage or a current with respect to a specific waveform by a photo-detector may be represented by an Equation configured of an average value $I'_0$ (or also called a 0 order Fourier coefficient) of the light intensity, Fourier coefficients $A'_D$ and $B'_D$, a reference angular velocity ω, and N, which is a natural number indicating the highest order among normalized Fourier coefficient that is not 0, as in Equation 1:

[Equation 1]

$$I_{ex}(t) = I'_0 + \sum_{D=1}^{N}[A'_D \cos(n\omega t) + B'_D \sin(n\omega t)]. \quad (1)$$

Since the components 21 of a Mueller-matrix for the sample 20 may be calculated from the Fourier coefficients $I'_0$, $A'_D$, and $B'_D$, it is very important in the dual optical element rotation type ellipsometer to more accurately measure values of the Fourier coefficients from the waveform of the light intensity measured by the photo-detector as in Equation 1.

In measurement for components 21 of a 4×4 Mueller-matrix of the sample 20 using the rotating-polarizer rotating-analyzer ellipsometer according to the related art, in the case in which an angular velocity of the polarizer 13 rotating at a constant velocity in the polarization modifying unit 12 is set to $\omega_P$, an angular velocity of the analyzer 33 rotating at a constant velocity in the polarization analyzing unit 31 is set to $\omega_A$, and an angular velocity ratio between them is constantly maintained as in $\omega_P:\omega_A=1:3$, when a reference angular velocity in Equation 1 is determined to $\omega=\omega_P$, a value of N becomes 8, such that a total of nine even number order Fourier coefficients may be measured. Therefore, as shown in FIG. 2, only nine components $M_{ij}$; i, j=1, 2, 3 among a total of sixteen components $M_{ij}$; i, j=1, 2, 3, 4 of the Mueller-matrix for the sample 20 are measurable values 21, and remaining seven components $M_{14}$, $M_{24}$, $M_{34}$, $M_{41}$, $M_{42}$, $M_{43}$, $M_{44}$ are non-measurable values 22.

In measurement for components 21 of a 4×4 Mueller-matrix of the sample 20 using the rotating-compensator rotating-analyzer ellipsometer according to the related art, in the case in which an angular velocity of the first compensator 14 rotating at a constant velocity in the polarization modifying unit 12 is set to $\omega_{C_1}$, an angular velocity of the analyzer 33 rotating at a constant velocity in the polarization analyzing unit 31 is set to $\omega_A$, and an angular velocity ratio between them is constantly maintained as in $\omega_{C_1}:\omega_A=3:1$, when a reference angular velocity in Equation 1 is determined to $\omega=\omega_A$, a value of N becomes 14, such that a total of fifteen even number order Fourier coefficients may be measured. Therefore, as shown in FIG. 3, only twelve components $M_{ij}$, i=1, 2, 3, j=1, 2, 3, 4 among a total of sixteen components $M_{ij}$; i, j=1, 2, 3, 4 of the Mueller-matrix for the sample 20 are measurable values 21, and remaining four components $M_{41}$, $M_{42}$, $M_{43}$, $M_{44}$ are non-measurable values 22.

In measurement for components 21 of a 4×4 Mueller-matrix of the sample 20 using the rotating-polarizer rotating-compensator ellipsometer according to the related art, in the case in which an angular velocity of the polarizer 13 rotating at a constant velocity in the polarization modifying unit 12 is set to $\omega_P$, an angular velocity of the second compensator 34 rotating at a constant velocity in the polarization analyzing unit 31 is set to $\omega_{C_2}$, and an angular velocity ratio between them is constantly maintained as in $\omega_{C_2}:\omega_P=3:1$, when a reference angular velocity in Equation 1 is determined to $\omega=\omega_P$, a value of N becomes 14, such that a total of fifteen even number order Fourier coefficients may be measured. Therefore, as shown in FIG. 4, only twelve components $M_{ij}$; i=1,2,3,4, j=1, 2, 3 among a total of sixteen components $M_{ij}$; i, j=1, 2, 3, 4 of the Mueller-matrix for the sample 20 are measurable values 21, and remaining four components $M_{14}$, $M_{24}$, $M_{34}$, $M_{44}$ are non-measurable values 22.

In measurement for components 21 of a 4×4 Mueller-matrix of the sample 20 using the dual-rotating-compensator ellipsometer according to the related art, in the case in which an angular velocity of the first compensator 14 rotating at a constant velocity in the polarization modifying unit 12 is set to $\omega_{C_1}$, an angular velocity of the second compensator 34 rotating at a constant velocity in the polarization analyzing unit 31 is set to $\omega_{C_2}$, and an angular velocity ratio between them is constantly maintained as in $\omega_{C_1}:\omega_{C_2}=1:5$, when a reference angular velocity in Equation 1 is determined to $\omega=\omega_{C_1}$, a value of N becomes 24, such that a total of twenty five even number order Fourier coefficients may be measured. Therefore, from sixteen or more selected among measured values of a total of twenty five Fourier coefficients, as shown in FIG. 5, all of a total of sixteen components $M_{ij}$; i, j=1, 2, 3, 4 of the Mueller-matrix for the sample 20 are measurable values 21.

The dual optical element rotation type ellipsometers according to the related art except for the dual-rotating-compensator ellipsometer according to the related art have a problem that residual polarization of the light source and polarization dependence of the photo-detector cause an error of measurement. In order to completely solve this problem, both of the polarizer and the analyzer 33 should be in a stop state at a designated azimuth angle at the time of measurement.

In the case of a single polarizer rotation type ellipsometer and a single analyzer rotation type ellipsometer mainly used in single optical element rotation type ellipsometers according to the related art, the Fourier coefficients that are measured in Equation 1 and are not zero are ($I'_0$, $A'_2$, $B'_2$), and in the case of a single compensator rotation type ellipsometer, the Fourier coefficients that are measured in Equation 1 and are not zero are ($I'_0$, $A'_2$, $B'_2$, $A'_4$, $B'_4$). Therefore, the number of components of the Mueller-matrix to be measured is larger than that of measured values, such that it is impossible to calculate the components of the Mueller-matrix from the measured Fourier coefficients by a general method. On the other hand, in the dual optical element rotation type ellipsometers according to the related art capable of measuring some or all of the components of the Mueller-matrix, since a value of N is relatively larger as compared with the single optical element rotation type ellipsometers, Fourier coefficients of high frequency components by a change in an azimuth angle of an optical element rotating at a constant velocity in Equation 1 should be measured. Therefore, a measurement equation and a correction method are complicated. Particularly, in the case of the dual-rotating-compensator ellipsometer according to the related art capable of measuring all of the components of the Mueller-matrix, it has been generally well-known that since even Fourier coefficients of a high order term in Equation 1 should be measured, accuracy and precision in measuring the Fourier coefficients are relatively lower as compared with the single optical element rotation type ellipsometers. On the other hand, as a gradual miniaturization technology and a three-dimensionally complicated nano-structure are adopted in the nano-element manufacturing technology, a demand for gradual improvement of measurement accuracy and measurement precision in measuring shapes and physical properties of nano-patterns using the dual optical element rotation type ellipsometers according to the related art has increased in the nano-element industry fields.

Therefore, the development of Mueller-matrix ellipsometers capable of solving the above-mentioned problems has been demanded.

RELATED ART DOCUMENT

Patent Document

Patent Document 1: U.S. Pat. No. 4,306,809
Patent Document 2: US 2007/0229826
Patent Document 3: U.S. Pat. No. 7,277,172
Patent Document 4: U.S. Pat. No. 7,224,471
Patent Document 5: U.S. Pat. No. 7,414,733
Patent Document 6: US 2011/0080585
Patent Document 7: U.S. Pat. No. 7,990,549
Patent Document 8: U.S. Pat. No. 8,446,584

Paper Document

Paper Document 1: D. E. Aspnes et. al., "Rotating-compensator/analyzer fixed-analyzer ellipsometer: Analysis and comparison to other automatic ellipsometers," J. Opt. Soc. Am. 66, 949 (1976).
Paper Document 2: R. M. A. Azzam, "Photopolarimeter using two modulated optical rotators," Opt. Lett. 5, 181 (1977).
Paper Document 3: R. M. A. Azzam, "Photopolarimetric measurement of the Mueller-matrix by Fourier analysis of a single detected signal," Opt. Lett. 6, 148 (1978).
Paper Document 4: P. S. Hauge, "Recent development in instrumentation in ellipsometry," Surf. Sci. 96, 108 (1980).

DISCLOSURE

Technical Problem

An object of the present invention is to provide an optical element rotation type Mueller-matrix ellipsometer capable of more accurately and precisely measuring components of a Mueller-matrix for samples by solving a problem that measurement accuracy and measurement precision are decreased due to residual polarization of a light source, polarization dependence of a photo-detector, measurement of Fourier coefficients of a high order term, and the like, in dual optical element rotation type ellipsometers according to the related art capable of measuring some or all of components of a Mueller-matrix for any sample.

Technical Solution

In one general aspect, an optical element rotation type Mueller-matrix ellipsometer includes: a light source emitting incident light toward a sample; a polarization modifying unit disposed between the light source and the sample on a movement path of the incident light, controlling a polarization state of the incident light emitted from the light source, and including a plurality of optical elements including a constant velocity rotation optical element rotating at a constant velocity and a scanning optical element; a polarization analyzing unit receiving reflected light (or transmitted light), analyzing a change in a polarization state of the reflected light (or the transmitted light), and including a plurality of optical elements including a constant velocity rotation optical element rotating at a constant velocity and a scanning optical element, the polarization state of the reflected light (or the transmitted light) being changed from that of the incident light polarized while passing through the polarization modifying unit due to reflection (or transmission) of the sample; a photo-detector receiving the reflected light (or the transmitted light) passing through the polarization analyzing unit and measuring intensity of the received light as an electrical signal such as a voltage or a current; a calculating device measuring and storing Fourier coefficient values of a waveform of light intensity depending on a change in an azimuth angle of the constant velocity rotation optical element by the photo-detector, calculating Fourier coefficient values for an azimuth angle of the scanning optical element from the measured Fourier coefficient values depending on the change in the azimuth angle of the constant velocity rotation optical element, and calculating components of a Mueller-matrix for the sample from the calculated Fourier coefficient values for the azimuth angle of the scanning optical element; and a computer controlling the azimuth angle of the scanning optical element, storing values of the components of the Mueller-matrix calculated from the calculating device as a file, and displaying the values of the components of the Mueller-matrix on a screen.

When the waveform [$I(\theta_r, \theta_s)$] of the light intensity measured by the photo-detector depending on the change in the azimuth angle of the constant velocity rotation optical element is as follows:

$$I(\theta_r, \theta_s) = I_0(\theta_s) + \sum_{n=1}^{N} [A_n(\theta_s)\cos(n\theta_r) + B_n(\theta_s)\sin(n\theta_r)],$$

{$\theta_r$: the azimuth angle of the constant velocity rotation optical element, $\theta_s$: the azimuth angle of the scanning optical element, $I_0(\theta_s)$: an average value of the light intensity or a zero order Fourier coefficient of the waveform of the light intensity depending on the change in the azimuth angle of the constant velocity rotation optical element, $A_D(\theta_s)$ and $B_D(\theta_s)$: Fourier coefficients of the waveform of the light intensity depending on the change in the azimuth angle of the constant velocity rotation optical element, $$I_0(\theta_s) = d_0 + \sum_{r=1}^{R} [d_r\cos(2r\theta_s) + d_{R+r}\sin(2r\theta_s)].$$

$$A_n(\theta_s) = A_{n,0} + \sum_{r=1}^{R} [A_{n,r}\cos(2r\theta_s) + A_{n,R+r}\sin(2r\theta_s)].$$

$$B_n(\theta_s) = B_{n,0} + \sum_{r=1}^{R} [B_{n,r}\cos(2r\theta_s) + B_{n,R+r}\sin(2r\theta_s)].$$

$d_r, A_{D,r}, B_{D,r}$ (r=0, 1, . . . , 2R): Fourier coefficients for the azimuth angle of the scanning optical element, N: order number of highest order among Fourier coefficients of $A_D(\theta_s)$ and $B_D(\theta_s)$ that that are not 0, R: order number of highest order among Fourier coefficients of $d_r$, $A_{D,r}$, and $B_{D,r}$ that are not 0}, Fourier coefficients $[I_0(\theta_{s,i}), A_D(\theta_{s,i}), B_D(\theta_{s,i})$; n=1, ..., N j=1, ..., j] of the waveform of the light intensity for the change in the azimuth angle of the constant velocity rotation optical element may be measured in a state in which the azimuth angle of the scanning optical element of $2\pi$ are divided j times at the same interval and the scanning optical element moves to and stops at each azimuth angle position $[\theta_{s,i}=2\pi(j-1)/J, (j=1, \ldots, J)]$, values of Fourier coefficients $(d_r, A_{D,r}, B_{D,r}; n=1, \ldots N, r=0, 1, \ldots, 2R)$ for the azimuth angle of the scanning optical element from measured values of the Fourier coefficients of the waveform of the light intensity for the change in the azimuth angle of the constant velocity rotation optical element may be calculated using discrete Fourier transformer as follows:

$$d_0 = \frac{1}{J} \sum_{j=1}^{J} I_0(\theta_{s,j}),$$

$$d_r = \frac{2}{J} \sum_{j=1}^{J} I_0(\theta_{s,j})\cos(2r\theta_{s,j}),$$

$$d_{R+r} = \frac{2}{J} \sum_{j=1}^{J} I_0(\theta_{s,j})\sin(2r\theta_{s,j}),$$

$$A_{n,0} = \frac{1}{J} \sum_{j=1}^{J} A_n(\theta_{s,j}),$$

$$A_{n,r} = \frac{2}{J} \sum_{j=1}^{J} A_n(\theta_{s,j})\cos(2r\theta_{s,j}),$$

$$A_{n,R+r} = \frac{2}{J} \sum_{j=1}^{J} A_n(\theta_{s,j})\sin(2r\theta_{s,j}),$$

$$B_{n,0} = \frac{1}{J} \sum_{j=1}^{J} B_n(\theta_{s,j}),$$

$$B_{n,r} = \frac{2}{J} \sum_{j=1}^{J} B_n(\theta_{s,j})\cos(2r\theta_{s,j}),$$

$$B_{n,R+r} = \frac{2}{J} \sum_{j=1}^{J} B_n(\theta_{s,j})\sin(2r\theta_{s,j}),$$

and the components of the Mueller-matrix for the sample may be calculated from the calculated values of Fourier coefficients for the azimuth angle of the scanning optical element.

The polarization modifying unit may be configured of one polarizer, the polarization analyzing unit may be configured of one analyzer, and the polarizer and the analyzer may be selected as the constant velocity rotation optical element and the scanning optical element, respectively, at the time of measurement.

The polarization modifying unit may be configured of one polarizer, the polarization analyzing unit may be configured of one analyzer, the optical element rotation type Mueller-matrix ellipsometer may further include a second polarizer disposed between the light source and the polarizer on an axis line of the incident light, and the polarizer and one of the analyzer and the second polarizer may be selected as the constant velocity rotation optical element and the scanning optical element, respectively, at the time of measurement.

The polarization modifying unit may be configured of one polarizer, the polarization analyzing unit may be configured of one analyzer, and the analyzer and the polarizer may be selected as the constant velocity rotation optical element and the scanning optical element, respectively, at the time of measurement.

The polarization modifying unit may be configured of one polarizer, the polarization analyzing unit may be configured of one analyzer, the optical element rotation type Mueller-matrix ellipsometer may further include a second analyzer disposed between the analyzer and the photo-detector on an axis line of the reflected light or the transmitted light, and the analyzer and one of the polarizer and the second analyzer may be selected as the constant velocity rotation optical element and the scanning optical element, respectively, at the time of measurement.

The polarization modifying unit may be configured of one polarizer and one compensator, the polarization analyzing unit may be configured of one analyzer, the polarizer may be disposed between the light source and the sample on an axis line of the incident light, the compensator may be disposed between the polarizer and the sample on the axis line of the incident light, and the compensator and one of the polarizer and the analyzer may be selected as the constant velocity rotation optical element and the scanning optical element, respectively, at the time of measurement.

The polarization modifying unit may be configured of one polarizer, the polarization analyzing unit may be configured of one compensator and one analyzer, the compensator may be disposed between the sample and the photo-detector on an axis line of the reflected light or the transmitted light, the analyzer may be disposed between the compensator and the photo-detector on the axis line of the reflected light or the transmitted light, the compensator and one of the polarizer and the analyzer may be selected as the constant velocity rotation optical element and the scanning optical element, respectively, at the time of measurement.

The polarization modifying unit may be configured of one polarizer and a first compensator, the polarization analyzing unit may be configured of a second compensator and one analyzer, the polarizer may be disposed between the light source and the sample on an axis line of the incident light, the first compensator may be disposed between the polarizer and the sample on the axis line of the incident light, the second compensator may be disposed between the sample and the photo-detector on an axis line of the reflected light or the transmitted light, the analyzer may be disposed between the second compensator and the photo-detector on the axis line of the reflected light or the transmitted light, one of the first compensator and the second compensator may be selected as the constant velocity rotation optical element and one of the remaining optical elements other than the constant velocity rotation optical element may be selected as the scanning optical element, at the time of measurement.

The optical element rotation type Mueller-matrix ellipsometer may analyze various physical properties including an interface property, a thickness of a thin film, a complex refractive index, a nano shape, an anisotropic property, a surface roughness, a composition ratio, and crystallinity of the sample from the measured Fourier coefficients and the measured components of the Mueller-matrix for the sample, and may be utilized as a physical property measuring apparatus including a measurement equipment for a semiconductor element process, a measurement equipment for a flat panel display process, a measurement equipment of a solar element, a thin film optical measurement equipment, a bio sensor, or a gas sensor.

Measurement data of the measured Fourier coefficients or the measured components of the Mueller-matrix for the sample may be obtained, an optical theoretical equation for the sample may be established and data of the Fourier coefficients or the components of the Mueller-matrix calculated using a plurality of unknown parameters for a set region may be obtained with respect to the established theoretical equation, and continuous functions for unknown parameters may be obtained from the data obtained by the calculation and be then optimized with respect to the measurement data using a least squares algorithm to obtain physical properties of the sample.

The light source may be selected among a xenon lamp, a tungsten-halogen lamp, a deuterium lamp, a transfer of the light emitted from the lamp through an optical fiber, gas laser, and a laser diode.

A spectrometer, which is one among photo-detectors formed of a charge coupled device (CCD), a complementary metal oxide semiconductor (CMOS), or a photodiode element, and including a plurality of pixels arranged in a linear structure or a two-dimensional plane structure, may be selected or a photo-detector formed of a photomultiplier tube (PMT) and a photodiode may be selected as the photo-detector.

The optical element rotation type Mueller-matrix ellipsometer may further include: a focus optical system allowing the incident light to be focused on the sample; and a collimator again changing the light reflected or transmitted by the sample into parallel light, wherein the focus optical system and the collimator are formed of one or more mirrors, one or more lenses made of heterogeneous materials, or an optical system including one or more mirrors and one or more lenses in order to correct chromatic aberration for a wide band wavelength, and uses the lenses or the mirrors coated with a single thin film or a multilayer thin film.

In another general aspect, a method for measuring a physical property of a sample using an optical element rotation type Mueller-matrix ellipsometer includes: a sample arranging step of mounting and arranging the sample; an azimuth angle setting step of setting azimuth angle values of a scanning optical element required in measurement; an initial value moving step of moving an azimuth angle of the scanning optical element into an initial value by a program command in a computer; a coefficient measuring step of measuring Fourier coefficients of a waveform of light intensity for a change in an azimuth angle of a constant velocity rotation optical element by a photo-detector; a final azimuth angle confirming step of confirming whether the azimuth angle of the scanning optical element arrives at a final target point; a scanning optical element moving step of moving and stopping the scanning optical element to and at another designated azimuth angle position and measuring Fourier coefficients for the azimuth angle of the constant velocity rotation optical element by the photo-detector, in the case in which the azimuth angle of the scanning optical element does not arrive at the final target point in the final azimuth angle confirming step; a Mueller-matrix calculating step of calculating components of a Mueller-matrix for the sample by calculating Fourier coefficients for the azimuth angle of the scanning optical element in the case in which the azimuth angle of the scanning optical element arrives at the final target point in the final azimuth angle confirming step; and a file storing step of storing the components of the Mueller-matrix calculated in the Mueller-matrix calculating step as a file in the computer or outputting the components of the Mueller-matrix on a screen.

Advantageous Effects

With the configuration as described above, in a single optical element rotation type Mueller-matrix ellipsometer according to an exemplary embodiment of the present invention, in order to overcome a decrease problem in measurement accuracy and measurement precision that occurs since relatively high order term components are included among Fourier coefficients obtained from a waveform of light intensity depending on a change in an azimuth angle of a constant velocity optical element measured by a photo-detector in a dual optical element rotation type Mueller-matrix ellipsometer according to the related art, components of Fourier coefficients of a low order term for a waveform of light intensity depending on a change in an azimuth angle of a scanning optical element are measured, and component values of a Mueller-matrix are calculated from the components of the Fourier coefficients of the low order term, thereby making it possible to improve measurement accuracy and measurement precision.

Further, in the single optical element rotation type Mueller-matrix ellipsometer according to the present invention, in the case of a single polarizer rotation type, a second polarizer is disposed between a light source and a polarizer, thereby making it possible to solve a residual polarization problem of the light source, and in the case of a single analyzer rotation type, a second analyzer is disposed between an analyzer and a photo-detector, thereby making it possible to solve a polarization dependence problem of the photo-detector. As a result, measurement accuracy may be improved.

DESCRIPTION OF DRAWINGS

The above and other objects, features and advantages of the present invention will become apparent from the following description of preferred embodiments given in conjunction with the accompanying drawings, in which.

DETAILED DESCRIPTION OF MAIN ELEMENTS

Figure 1:
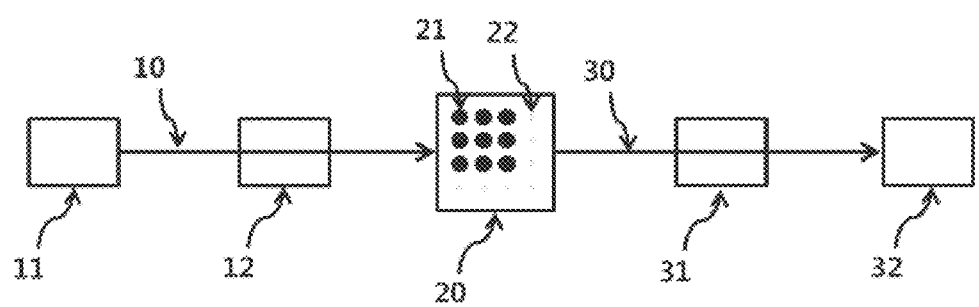
FIG. 1 is a schematic view of an optical element rotation type Mueller-matrix ellipsometer according to a first exemplary embodiment of the related art.
Figure 2:
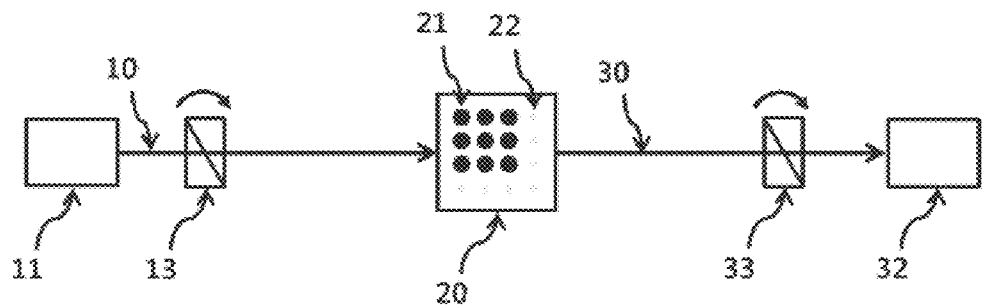
FIG. 2 is a schematic view of a rotating-polarizer rotating-analyzer Mueller-matrix ellipsometer according to a second exemplary embodiment of the related art.
Figure 3:
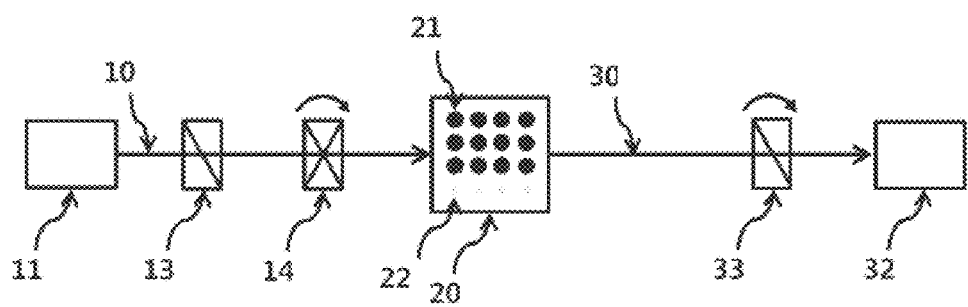
FIG. 3 is a schematic view of a rotating-compensator rotating-analyzer Mueller-matrix ellipsometer according to a third exemplary embodiment of the related art.
Figure 4:
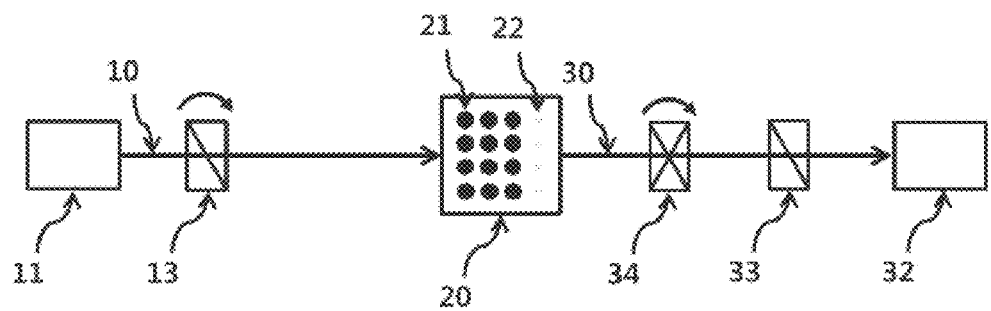
FIG. 4 is a schematic view of a rotating-polarizer rotating-compensator Mueller-matrix ellipsometer according to a fourth exemplary embodiment of the related art.
Figure 5:
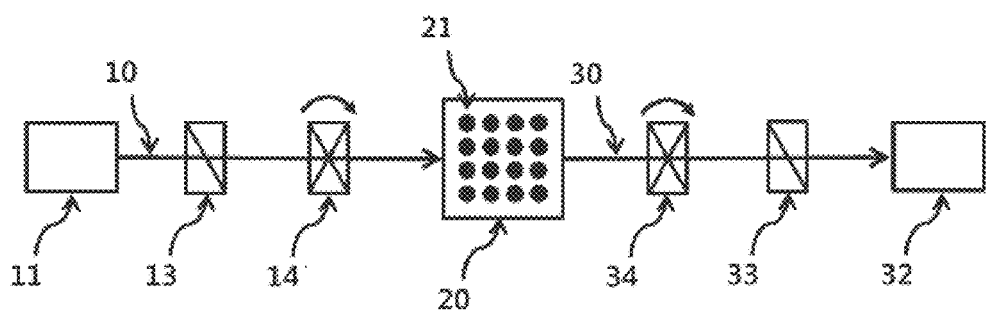
FIG. 5 is a schematic view of a dual-rotating-compensator ellipsometer Mueller-matrix ellipsometer according to a fifth exemplary embodiment of the related art.

100: Incident light
110: Light source
130: Polarizer
140: First compensator
150: Second polarizer
200: Sample
210: Components of Mueller-matrix for sample that are measurable
220: Components of Mueller-matrix for sample that are not measurable
300: Reflect light (or transmitted light)
320: Photo-detector
330: Analyzer
340: Second compensator
350: Second analyzer
500: Incident surface
510: Reference axis
520: Transmitted axis
530: fast axis of phase retarder of first compensator
540: fast axis of phase retarder of second compensator
550: Transmitted axis
610: Calculating device
620: Computer

BEST MODE

Hereinafter, exemplary embodiments will be described in detail with reference to the accompanying drawings so that they can be easily practiced by those skilled in the art to which the present invention pertains. However, in describing an operation principle of exemplary embodiments of the present invention, detailed descriptions of well-known functions or constructions will be omitted so as not to unnecessarily obscure the gist of the present invention.

In addition, parts performing similar functions and actions will be denoted by the same reference numerals throughout the accompanying drawings. In addition, unless explicitly described otherwise, "comprising" any components will be understood to imply the inclusion of other components but not the exclusion of any other components.

Hereinafter, configurations and functions of optical element rotation type Mueller-matrix ellipsometers according to exemplary embodiments of the present invention will be described. First, FIGS. 6 and 8 to 14 are views schematically showing configurations of single optical element rotation type Mueller-matrix ellipsometers according to the present invention for accomplishing the above-mentioned object.

The optical element rotation type Mueller-matrix ellipsometer according to the present invention is configured to include an optical source, a polarization modifying unit, a sample, a polarization analyzing unit, a photo-detector, a calculating device, and a computer.

The polarization modifying unit or the polarization analyzing unit is mounted with a plurality of optical elements.

The optical element is one optical element selected among a constant velocity optical element rotating at a constant velocity and remaining optical elements stopping at the time of measurement, and includes a scanning optical element moving to azimuth angles sequentially selected among a plurality of designated azimuth angles.

The optical element rotation type Mueller-matrix ellipsometer according to the present invention includes the calculating device calculating components of a Mueller-matrix for the sample from Fourier coefficients each measured for the plurality of azimuth angles for the scanning optical element and the computer capable of storing values of the calculated components of the Mueller-matrix as a data file.

In the case in which it is assumed that the optical element rotation type Mueller-matrix ellipsometer does not have an error, a theoretical equation for light intensity measured as an electrical signal such as a voltage or a current by the photo-detector with respect to any wavelength and any incident angle is the following Equation 2.

[Equation 2]

$$I_{th}(t) = I_0 + \sum_{n=1}^{N}[A_n\cos(n\omega t) + B_n\sin(n\omega t)]. \quad (2)$$

$I_0$: theoretical equation of average value (or also called 0 order Fourier coefficient) of light intensity $A_L$, $B_L$: theoretical equation of Fourier coefficients $\omega$: angular velocity of constant velocity optical element N: order number of highest order among Fourier coefficients that are not 0

The number of Fourier coefficient components that may be measured by the single optical element rotation type ellipsometer according to the related art is three such as $I_0$, $A_2$, and $B_2$ in the case of a single polarizer rotation type and a single analyzer rotation type and is five such as $I_0$, $A_2$, $B_2$, $A_4$, and $B_4$ in the case of a single compensator rotation type, while the numbers of components of a Mueller-matrix, which are unknown quantities, that should be finally obtained from an experiment using the two groups of ellipsometers are nine and twelve, respectively, which are larger than that of measured values. Therefore, values of the components of the Mueller-matrix may not be calculated from the measured values for the Fourier coefficients using the single optical element rotation type ellipsometer according to the related art.

When an azimuth angle of one optical element selected in order to change the azimuth angle, that is the scanning optical element, among the optical elements stopping at any azimuth angle when measuring the Fourier coefficients is denoted by $\theta_s$, a theoretical equation of the Fourier coefficients may be represented by a function of $\theta_s$ as follows.

$$I_0(\theta_s) = d_0 + \sum_{r=1}^{R} [d_r\cos(2r\theta_s) + d_{R+r}\sin(2r\theta_s)]. \quad (3)$$

$$A_n(\theta_s) = A_{n,0} + \sum_{r=1}^{R} [A_{n,r}\cos(2r\theta_s) + A_{n,R+r}\sin(2r\theta_s)]. \quad (4)$$

$$B_n(\theta_s) = B_{n,0} + \sum_{r=1}^{R} [B_{n,r}\cos(2r\theta_s) + B_{n,R+r}\sin(2r\theta_s)]. \quad (5)$$

Here, $(d_r, A_{D,r}, B_{D,r}; n=1 \ldots, N, r=0, 1, \ldots, 2R)$ are Fourier coefficients for the azimuth angle of the scanning optical element, are given as a function of the components of the Mueller-matrix for the sample and azimuth angles of the other stopping optical elements except for the scanning optical element, and are a function independent of $\theta_s$, and R0 is an order number of the highest order among Fourier coefficients of $(d_r, A_{D,r}, B_{D,r})$ that are not 0.

Therefore, when each of the Fourier coefficients is measured with respect to a plurality of azimuth angles $\theta_j$ arbitrarily selected for the scanning optical element, values of $(d_r, A_{D,r}, B_{D,r}, n=1 \ldots N, r=0, 1, \ldots, 2R)$ may be calculated from them.

For example, when Fourier coefficients $[I_0(\theta_{s,i}) A_D(\theta_{s,i}) B_D(\theta_{s,i})$ $n=1, \ldots, N$ $j=1, \ldots, j]$ of a waveform of light intensity for a change in an azimuth angle of the constant velocity rotation optical element are measured in a state in which an azimuth angle of the scanning optical element of $2\pi$ are divided j times at the same interval and the scanning optical element moves to and stops at each azimuth angle position $[\theta_{s,i}=2\pi(j-1)/J, (j=1, \ldots, J)]$, values of Fourier coefficients $(d_r A_{D,r} B_{D,I} n=1 \ldots N r=0, 1, \ldots, 2R)$ for the azimuth of the scanning optical element may be simply obtained from measured values of the Fourier coefficients of the waveform of the light intensity for the change in the azimuth angle of the constant velocity rotation optical element using discrete Fourier transformer as follows.

$$d_0 = \frac{1}{J}\sum_{j=1}^{J} I_0(\theta_{s,j}), \quad (6)$$

$$d_r = \frac{2}{J}\sum_{j=1}^{J} I_0(\theta_{s,j})\cos(2r\theta_{s,j}), \quad (7)$$

$$d_{R+r} = \frac{2}{J}\sum_{j=1}^{J} I_0(\theta_{s,j})\sin(2r\theta_{s,j}), \quad (8)$$

$$A_{n,0} = \frac{1}{J}\sum_{j=1}^{J} A_n(\theta_{s,j}), \quad (9)$$

$$A_{n,r} = \frac{2}{J}\sum_{j=1}^{J} A_n(\theta_{s,j})\cos(2r\theta_{s,j}), \quad (10)$$

$$A_{n,R+r} = \frac{2}{J}\sum_{j=1}^{J} A_n(\theta_{s,j})\sin(2r\theta_{s,j}), \quad (11)$$

$$B_{n,0} = \frac{1}{J}\sum_{j=1}^{J} B_n(\theta_{s,j}), \quad (12)$$

$$B_{n,r} = \frac{2}{J}\sum_{j=1}^{J} B_n(\theta_{s,j})\cos(2r\theta_{s,j}), \quad (13)$$

$$B_{n,R+r} = \frac{2}{J}\sum_{j=1}^{J} B_n(\theta_{s,j})\sin(2r\theta_{s,j}), \quad (14)$$

Figure 6:
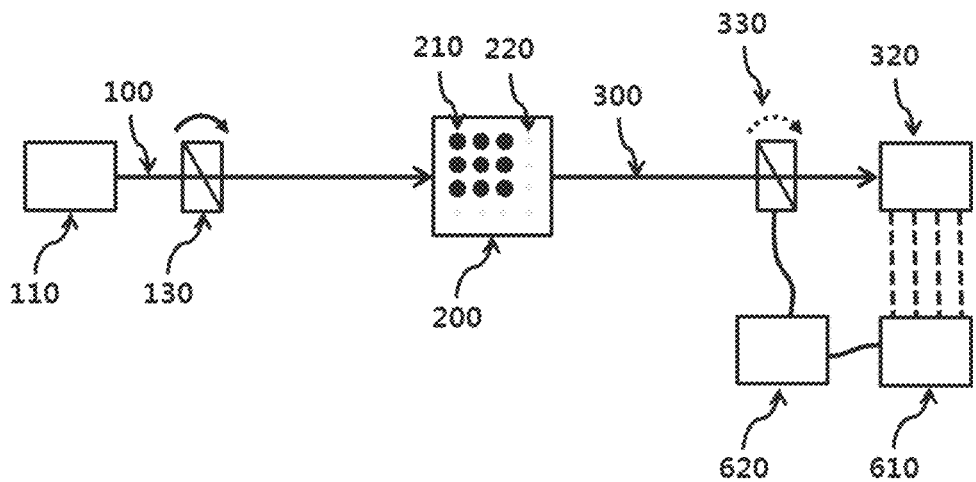
FIG. 6 is a schematic view of an optical element rotation type ellipsometer according to a first exemplary embodiment of the present invention.

Core components of an optical element rotation type Mueller-matrix ellipsometer according to a first exemplary embodiment of the present invention will be described with reference to FIG. 6.

A polarization modifying unit is configured of a polarizer 130, which is a component having a linear polarizer attached to a pupil axis constant velocity rotation motor.

A polarization analyzing unit is configured of an analyzer 330, which is a component having a linear polarizer attached to a pupil axis stepping motor.

The polarizer 130 may rotate at a constant velocity at the time of the measurement, while the analyzer 330 may stop at a set azimuth angle at the time of the measurement by remotely controlling the stepping motor using a computer 620.

The optical element rotation type Mueller-matrix ellipsometer according to a first exemplary embodiment of the present invention includes a light source 110 disposed on a line of incident light 100, the polarizer 130 disposed on the line of the incident light 100, disposed in the polarization modifying unit, which is an optical system allowing the incident light 100 emitted in parallel from the light source 110 toward a sample 200 to be in a specific polarization state, and rotating at a constant velocity at the time of the measurement, the analyzer 330 disposed on a line of reflected light (or transmitted light) 300, disposed in the polarization analyzing unit, which is an optical system analyzing a polarization state of the reflected light (or the transmitted light) 300, and stopping at a designated azimuth angle at the time of the measurement, a photo-detector 320 disposed on the line of the reflected light (or the transmitted light) 300 and measuring an amount of light passing through the analyzer 330 as an electrical signal such as a voltage or a current, and a calculating device 610 disposed on the line of the reflected light (or the transmitted light) 300 and measuring and storing Fourier coefficients for a light intensity signal waveform depending on a change in an azimuth angle of the polarizer 130 from a light intensity signal measured from the photo-detector 320.

Here, the pupil axis stepping motor attached to the analyzer 330 is remotely controlled using the computer 620 to change the azimuth angle of the analyzer 330 into another position and maintain the analyzer 330 in a stop state.

The analyzer 330 again measures the Fourier coefficients for the light intensity signal waveform at a changed new position and stores the measured Fourier coefficients in the calculating device 610.

A process of changing the azimuth angle of the analyzer 330 into a new position, measuring the Fourier coefficients for the light intensity signal waveform, and storing the measured Fourier coefficients in the calculating device 610 is repeated by a designated number.

Components 210 of the Mueller-matrix for the sample 200 may be calculated from a data set of the Fourier coefficients measured at a plurality of preset azimuth angles of the analyzer 330, using the calculating device 610, be stored as a file in the computer 620, and be displayed as a drawing on a screen of a monitor, if necessary.

Figure 7:
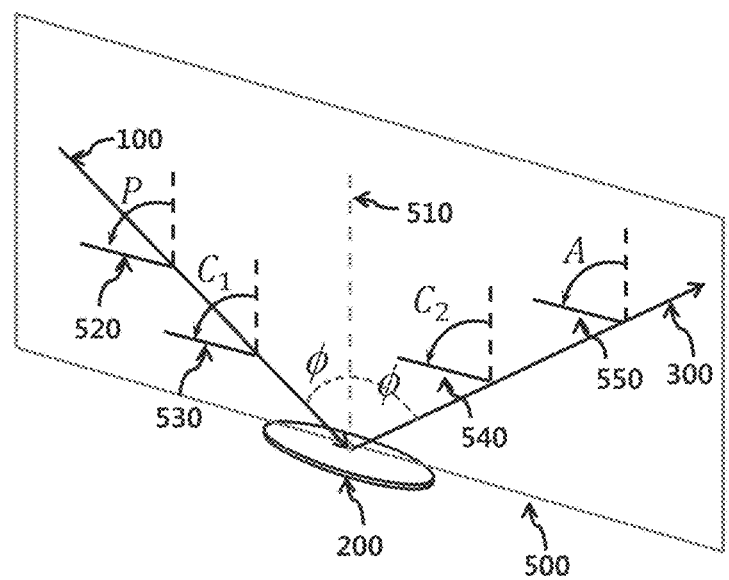
FIG. 7 is a conceptual diagram for describing azimuth angles of main optical elements used in the optical element rotation type ellipsometer according to the present invention.

FIG. 7 is a conceptual diagram for definitions of azimuth angles of the respective main optical elements used at the time of measuring a reflection type in the optical element rotation type Mueller-matrix ellipsometers.

A surface on which a path of the incident light 100 having an incident angle of φ and a path of the reflected light 300 having a reflected angle of φ are present among surfaces perpendicular to a surface of the sample 200 will be defined as an incident surface 500, and an axis perpendicular to the sample 200 will be defined as a reference axis 510.

Azimuth angles at which positions of a transmitted axis 520 of the linear polarizer in the polarizer 130 and a transmitted axis 550 of the linear polarizer in the analyzer 330 are measured in a direction as shown in FIG. 7 based on the incident surface 500 will be denoted by P and A, respectively.

Azimuth angles at which positions of a fast axis 530 of a phase retarder in the first compensator 140 and a fast axis 540 of a phase retarder in the second compensator 340 are measured based on the incident surface 500 will be denoted by $C_1$ and $C_2$, respectively.

In the optical element rotation type Mueller-matrix ellipsometer according to a first exemplary embodiment of the present invention, the Fourier coefficients of Equation 2 are represented by three simultaneous equations configured of a total of ten unknown quantities, that is, $g_0$, $M_{11}$, $M_{21}$, $M_{31}$, $M_{12}$, $M_{22}$, $M_{32}$, $M_{13}$, $M_{23}$, and $M_{33}$ as in the following Equations:

$$I_0 = g_0[M_{11} + M_{21} \cos(2A) + M_{31} \sin(2A)], \quad (15)$$

$$A_2 = g_0[M_{12} + M_{22} \cos(2A) + M_{32} \sin(2A)], \quad (16)$$

$$B_2 = g_0[M_{13} + M_{23} \cos(2A) + M_{33} \sin(2A)], \quad (17)$$

It may be appreciated that when the azimuth angle of the analyzer and the azimuth of the scanning optical element are selected as A and θ, respectively, in Equations 3 to 5, forms of the respective equations are divided into a term of a dc component, a term of cos(2A), and a term of sin (2A). Therefore, components of the Fourier coefficients for the azimuth angle A of the scanning optical element are given by nine simultaneous equations as follows:

$$d_0 = g_0 M_{11}, \quad (18)$$

$$d_1 = g_0 M_{21}, \quad (19)$$

$$d_2 = g_0 M_{31}, \quad (20)$$

$$A_{2,0} = g_0 M_{12}, \quad (21)$$

$$A_{2,1} = g_0 M_{22}, \quad (22)$$

$$A_{2,2} = g_0 M_{32}, \quad (23)$$

$$B_{2,0} = g_0 M_{13}, \quad (21)$$

$$B_{2,1} = g_0 M_{23}, \quad (22)$$

$$B_{2,2} = g_0 M_{33}, \quad (23).$$

Therefore, when Equations 18 to 23 are rearranged in connection with the components of the Mueller-matrix for any sample, the following equations are given:

$$M_{11} = \frac{d_0}{g_0}, \quad (24)$$

$$M_{12} = \frac{A_{2,0}}{g_0}, \quad (25)$$

-continued $$M_{13} = \frac{B_{2,0}}{g_0}, \quad (26)$$

$$M_{21} = \frac{d_1}{g_0}, \quad (27)$$

$$M_{22} = \frac{A_{2,1}}{g_0}, \quad (28)$$

$$M_{23} = \frac{B_{2,1}}{g_0}, \quad (29)$$

$$M_{31} = \frac{d_2}{g_0}, \quad (30)$$

$$M_{32} = \frac{A_{2,2}}{g_0}, \quad (31)$$

$$M_{33} = \frac{B_{2,2}}{g_0}, . \quad (32)$$

Here, $g_0$, which is a physical amount that may be measured using an experiment in a state in which the light source, the polarization modifying unit, the polarization analyzing unit, and the photo-detector are aligned in a row after the sample 200 is removed from the ellipsometer or any sample of which a structure and reflective index values of each layer are already known at any incident angle, which is associated with optical characteristics of a sample and a measuring equipment used at the time of the measurement.

When a value of $g_0$ is known by the method as described above, nine components ($M_{ij}$; i, j=1, 2, 3) among a total of sixteen components of the Mueller-matrix for the sample may be obtained from the measurement using Equations 24 to 32.

In addition, when each of Equations 25 to 32 is divided by a component $M_{11}$ of Equation 24, since the normalized components of the Mueller-matrix such as $m_{12} = M_{12}/M_{11}$, $m_{13} = M_{13}/M_{11}$, $m_{21} = M_{21}/M_{11}$, $m_{22} = M_{22}/M_{11}$, $m_{23} = M_{23}/M_{11}$, $m_{31} = M_{31}/M_{11}$, $m_{32} = M_{32}/M_{11}$, and $m_{33} = M_{33}/M_{11}$ are independent of the value of $g_0$, they may be obtained directly from the measurement.

Figure 8:
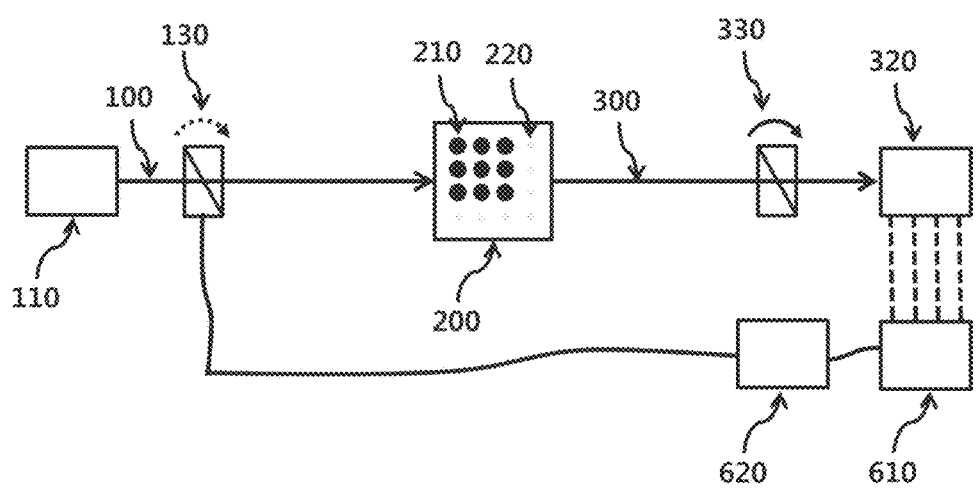
FIG. 8 is a schematic view of an optical element rotation type ellipsometer according to a second exemplary embodiment of the present invention.

Core components of an optical element rotation type Mueller-matrix ellipsometer according to a second exemplary embodiment of the present invention will be described with reference to FIG. 8.

The polarization modifying unit is configured of a polarizer 130, which is a component having a linear polarizer attached to a pupil axis stepping motor, the polarization analyzing unit is configured of an analyzer 330, which is a component having a linear polarizer attached to a pupil axis constant velocity rotation motor, and the analyzer 330 may rotate at a constant velocity at the time of the measurement, while the polarizer 130 may stop at a designated azimuth angle at the time of the measurement by remotely controlling the stepping motor using the computer 620.

In the optical element rotation type Mueller-matrix ellipsometer according to a second exemplary embodiment of the present invention, the Fourier coefficients of Equation 2 are represented by three simultaneous equations configured of a total of ten unknown quantities, that is, $g_0$, $M_{11}$, $M_{21}$, $M_{31}$, $M_{12}$, $M_{22}$, $M_{32}$, $M_{13}$, $M_{23}$, and $M_{33}$ as follows:

$$I_0 = g_0[M_{11} + M_{21} \cos(2P) + M_{131} \sin(2P)], \quad (33)$$

$$A_2 = g_0[M_{13} + M_{23} \cos(2P) + M_{33} \sin(2P)], \quad (34)$$

$$B_2 = g_0[M_{13} + M_{23} \cos(2P) + M_{33} \sin(2P)], \quad (35).$$

It may be appreciated that when the azimuth angle of the analyzer and the azimuth of the scanning optical element are selected as P and θ, respectively, in Equations 33 to 35, forms of the respective equations are divided into a term of a dc component, a term of cos(2P), and a term of sin(2P). Therefore, the components of the Mueller-matrix for any sample are given as follows from the components of the Fourier coefficients for the azimuth angle P of the scanning optical element:

$$M_{11} = \frac{d_0}{g_0}, \quad (36)$$

$$M_{12} = \frac{d_1}{g_0}, \quad (37)$$

$$M_{13} = \frac{d_2}{g_0}, \quad (38)$$

$$M_{21} = \frac{A_{2,0}}{g_0}, \quad (39)$$

$$M_{22} = \frac{A_{2,1}}{g_0}, \quad (40)$$

$$M_{23} = \frac{A_{2,2}}{g_0}, \quad (41)$$

$$M_{31} = \frac{B_{2,0}}{g_0}, \quad (42)$$

$$M_{32} = \frac{B_{2,1}}{g_0}, \quad (43)$$

$$M_{33} = \frac{B_{2,2}}{g_0}, . \quad (44)$$

Core components of an optical element rotation type Mueller-matrix ellipsometer according to a third exemplary embodiment of the present invention will be described with reference to FIGS. 9A and 9B.

The optical element rotation type Mueller-matrix ellipsometer according to a third exemplary embodiment of the present invention further includes a second polarizer 150 disposed between the light source 110 and the polarizer 130 rotating at a constant velocity on the axis line of the incident light 100, such that it includes three linear polarizers.

Figure 9A:
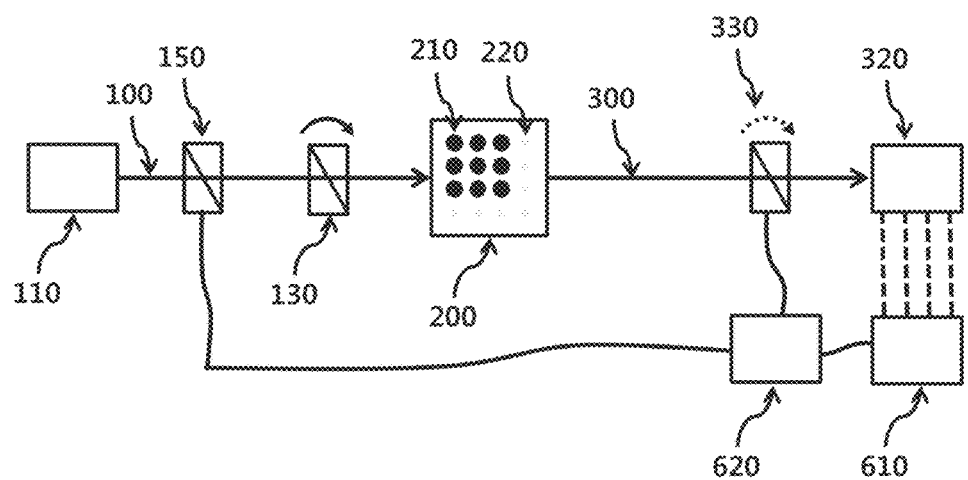
FIGS. 9A and 9B are schematic views of an optical element rotation type ellipsometer according to a third exemplary embodiment of the present invention.
Figure 9B:
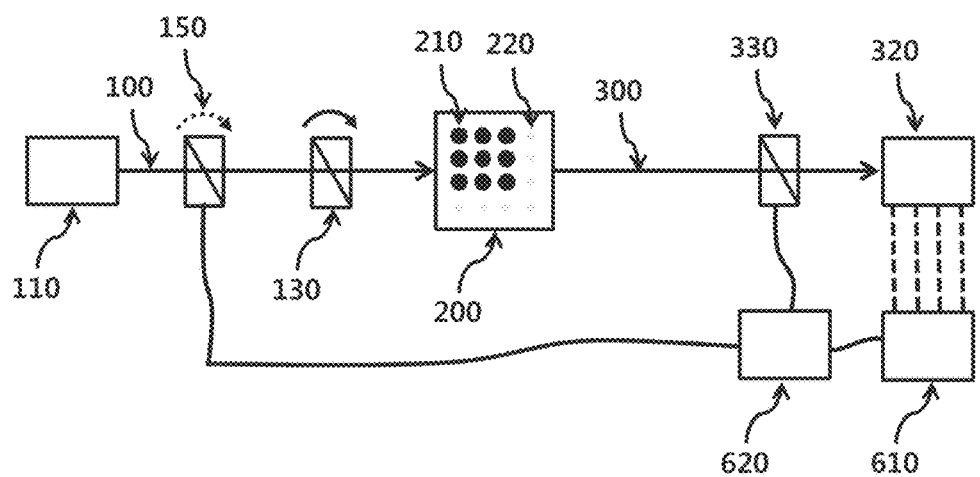

In this case, the analyzer 330 may be selected as the scanning optical element, as shown in FIG. 9A, or the second polarizer 150 that is newly added may be selected as the scanning optical element, as shown in FIG. 9B, and the scanning optical element has an azimuth angle that may be remotely controlled by the computer 620 and stops at a set position at the time of the measurement.

In addition, the optical element rotation type Mueller-matrix ellipsometer according to a third exemplary embodiment of the present invention may obtain values of nine components of the Mueller-matrix for the sample 200 from an experiment when a method of finding a solution of simultaneous equations using Equations 6 to 14 is used. A result thereof was omitted for convenience.

Core components of an optical element rotation type Mueller-matrix ellipsometer according to a fourth exemplary embodiment of the present invention will be described with reference to FIGS. 10A and 10B.

The optical element rotation type Mueller-matrix ellipsometer according to a fourth exemplary embodiment of the present invention further includes a second analyzer 350 disposed between the analyzer 300 rotating at the constant velocity and the photo-detector 320 on the axis line of the reflected light (or the transmitted line) 300, such that it includes three linear polarizers.

Figure 10A:
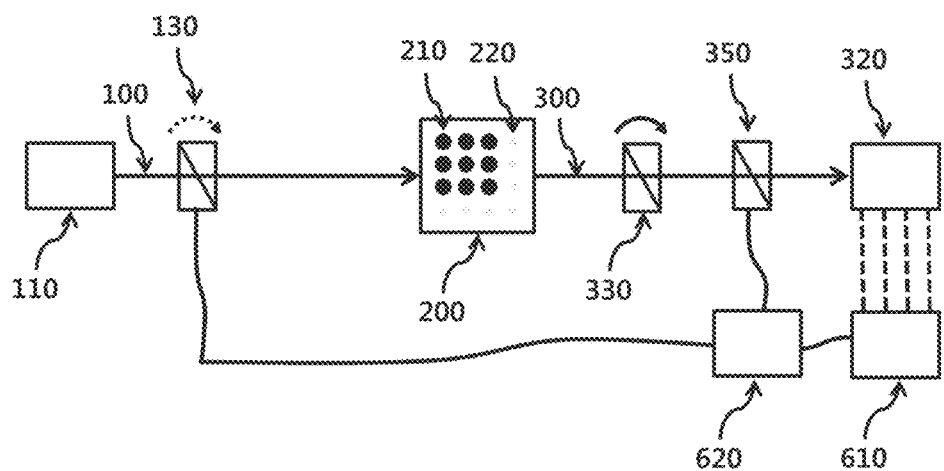
FIGS. 10A and 10B are schematic views of an optical element rotation type ellipsometer according to a fourth exemplary embodiment of the present invention.
Figure 10B:
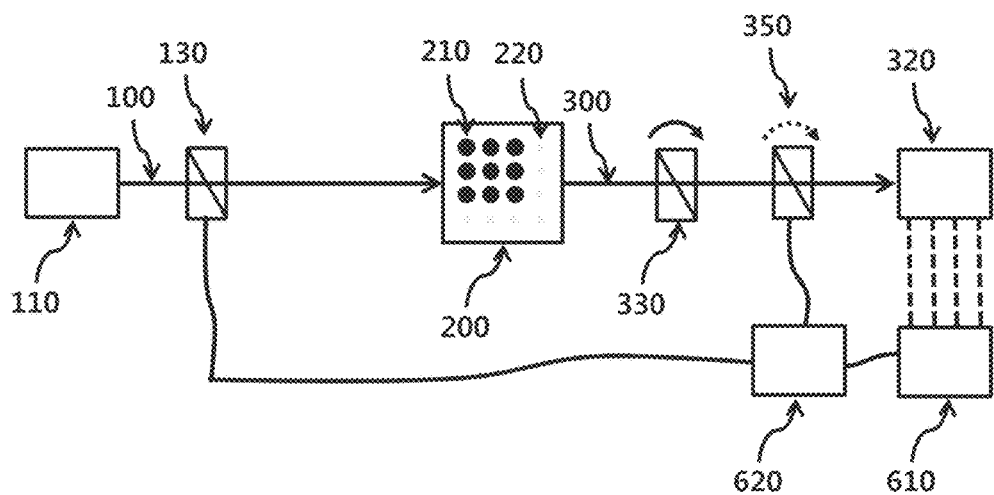

In this case, the polarizer 130 may be selected as the scanning optical element, as shown in FIG. 10A, or the second analyzer 350 that is newly added may be selected as the scanning optical element, as shown in FIG. 10B, and the scanning optical element has an azimuth angle that may be remotely controlled by the computer 620 and stops at a set position at the time of the measurement.

Values of nine components of the Mueller-matrix for the sample may be obtained from an experiment when the method of finding the solution of the simultaneous equations using Equations 6 to 14 is used. A result thereof was omitted for convenience.

Core components of an optical element rotation type Mueller-matrix ellipsometer according to a fifth exemplary embodiment of the present invention will be described with reference to FIGS. 11A and 11B.

In the optical element rotation type Mueller-matrix ellipsometer according to a fifth exemplary embodiment of the present invention, the polarization modifying unit includes a polarizer 130, which is a component having a linear polarizer attached to a pupil axis stepping motor, and a first compensator 140, which is a component having a phase retarder attached to a pupil axis constant velocity rotation motor, and the polarization analyzing unit includes an analyzer 330, which is a component having a linear polarizer attached to the pupil axis stepping motor.

In addition, the first compensator 140 may rotate at a constant velocity at the time of the measurement, while the polarizer 130 and the analyzer 330 may stop at designated azimuth angles at the time of the measurement by remotely controlling the stepping motor using the computer 620.

Figure 11A:
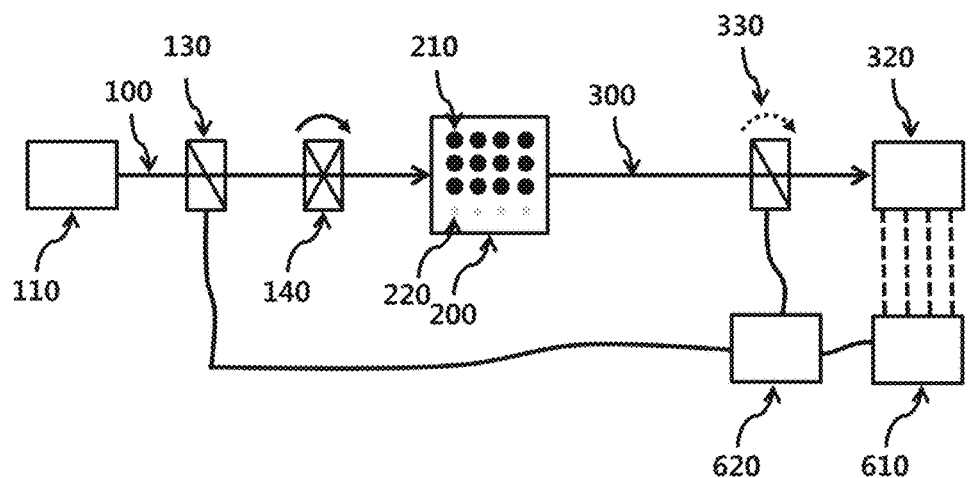
FIGS. 11A and 11B are schematic views of an optical element rotation type ellipsometer according to a fifth exemplary embodiment of the present invention.
Figure 11B:
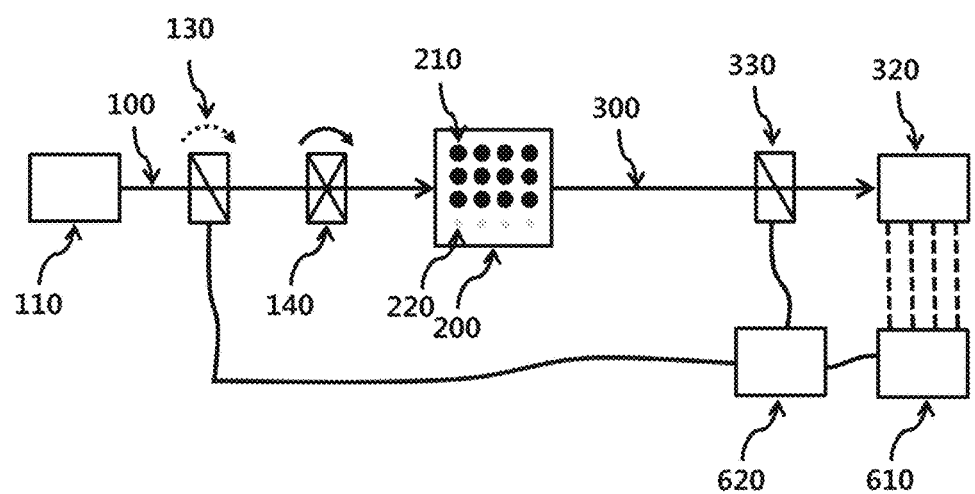

In this case, the analyzer 330 may be selected as the scanning optical element, as shown in FIG. 11A, or the polarizer 130 may be selected as the scanning optical element, as shown in FIG. 11B, and values of twelve components of the Mueller-matrix for the sample may be obtained from an experiment when the method of finding the solution of the simultaneous equations using Equations 6 to 14 is used. A result thereof was omitted for convenience.

Core components of an optical element rotation type Mueller-matrix ellipsometer according to a sixth exemplary embodiment of the present invention will be described with reference to FIGS. 12A and 12B.

In the optical element rotation type Mueller-matrix ellipsometer according to a sixth exemplary embodiment of the present invention, the polarization modifying unit is configured of a polarizer 130, which is a component having a linear polarizer attached to a pupil axis stepping motor, and the polarization analyzing unit is configured of a second compensator 340, which is a component having a phase retarder attached to a pupil axis constant velocity rotation motor, and an analyzer 330, which is a component having a linear polarizer attached to the pupil axis stepping motor.

In addition, the second compensator 340 may rotate at a constant velocity at the time of the measurement, while the polarizer 130 and the analyzer 330 may stop at designated azimuth angles at the time of the measurement by remotely controlling the stepping motor using the computer 620.

Figure 12A:
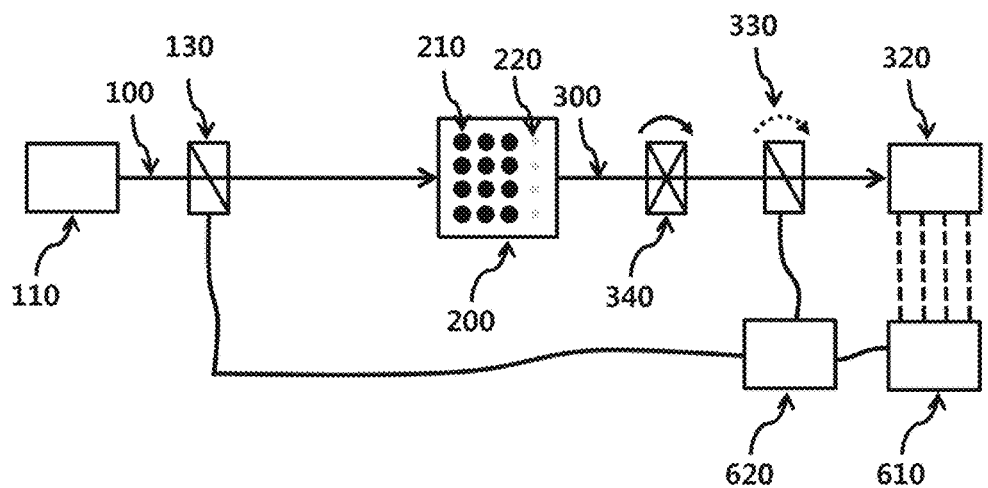
FIGS. 12A and 12B are schematic views of an optical element rotation type ellipsometer according to a sixth exemplary embodiment of the present invention.
Figure 12B:
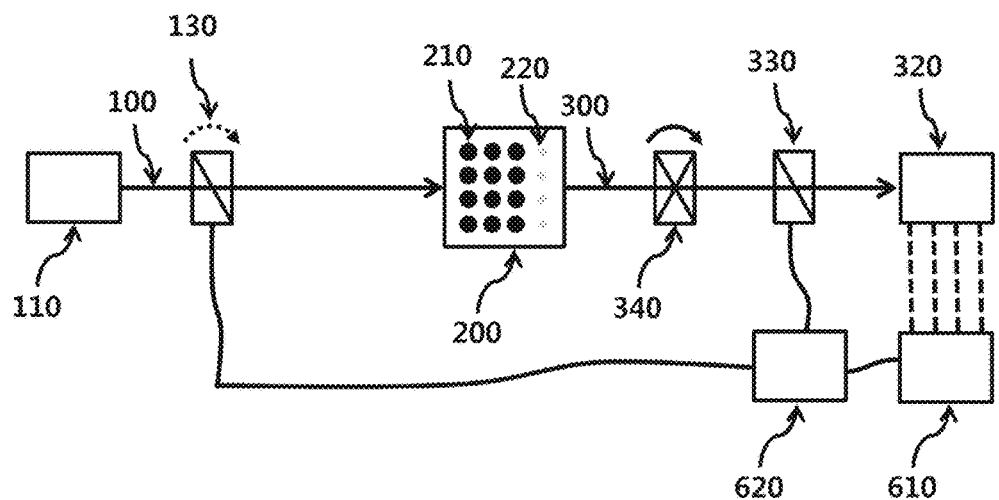

In this case, the analyzer 330 may be selected as the scanning optical element, as shown in FIG. 12A, or the polarizer 130 may be selected as the scanning optical element, as shown in FIG. 12B, and values of twelve components of the Mueller-matrix for the sample may be obtained from an experiment when the method of finding the solution of the simultaneous equations using Equations 6 to 14 is used. A result thereof was omitted for convenience.

Core components of an optical element rotation type Mueller-matrix ellipsometer according to a seventh exemplary embodiment of the present invention will be described with reference to FIG. 13.

In the optical element rotation type Mueller-matrix ellipsometer according to a seventh exemplary embodiment of the present invention, the polarization modifying unit is configured of a polarizer 130, which is a component having a linear polarizer attached to a pupil axis stepping motor, and a first compensator 140, which is a component having a phase retarder attached to the pupil axis stepping motor, and the polarization analyzing unit is configured of a second compensator 340, which is a component having a phase retarder attached to a pupil axis constant velocity rotation motor, and an analyzer 330, which is a component having a linear polarizer attached to the pupil axis stepping motor.

In addition, the second compensator 340 may rotate at a constant velocity at the time of the measurement, while the polarizer 130, the first compensator 140, and the analyzer 330 may stop at designated azimuth angles at the time of the measurement by remotely controlling the stepping motor using the computer 620.

Figure 13:
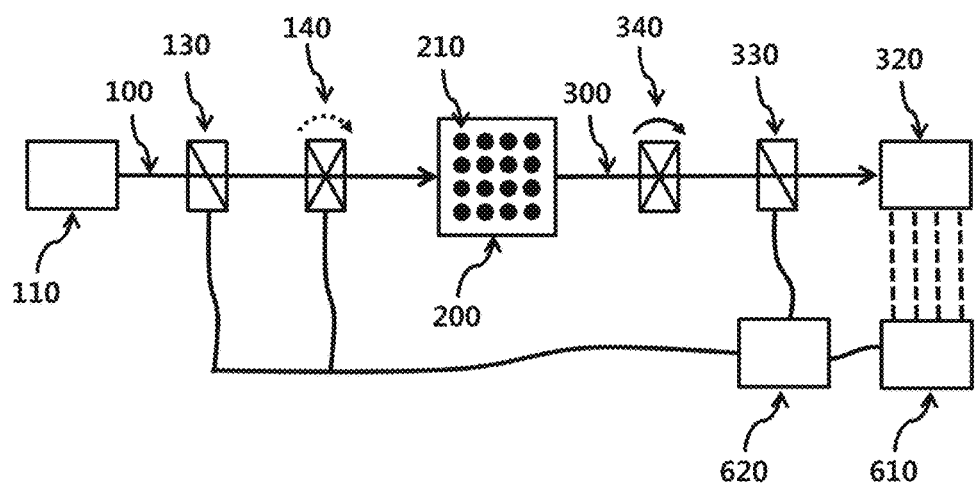
FIG. 13 is a schematic view of an optical element rotation type ellipsometer according to a seventh exemplary embodiment of the present invention.

In this case, when the first compensator 140 is selected as the scanning optical element as shown in FIG. 13, all of sixteen components of the Mueller-matrix for the sample may be obtained using the method of finding the solution of the simultaneous equations using Equations 6 to 14. However, when the polarizer 130 or the analyzer 330 is selected as the scanning optical element in FIG. 13, only twelve components, which are some of components of the Mueller-matrix for the sample may be obtained from the measurement. A result thereof was omitted for convenience.

Core components of an optical element rotation type Mueller-matrix ellipsometer according to an eighth exemplary embodiment of the present invention will be described with reference to FIG. 14.

In the optical element rotation type Mueller-matrix ellipsometer according to an eighth exemplary embodiment of the present invention, the polarization modifying unit is configured of a polarizer 130, which is a component having a linear polarizer attached to a pupil axis stepping motor, and a first compensator 140, which is a component having a phase retarder attached to a pupil axis constant velocity rotation motor, and the polarization analyzing unit is configured of a second compensator 340, which is a component having a phase retarder attached to the pupil axis stepping motor, and an analyzer 330, which is a component having a linear polarizer attached to the pupil axis stepping motor.

In addition, the first compensator 140 may rotate at a constant velocity at the time of the measurement, while the polarizer 130, the second compensator 340, and the analyzer 330 may stop at designated azimuth angles at the time of the measurement by remotely controlling the stepping motor using the computer 620.

Figure 14:
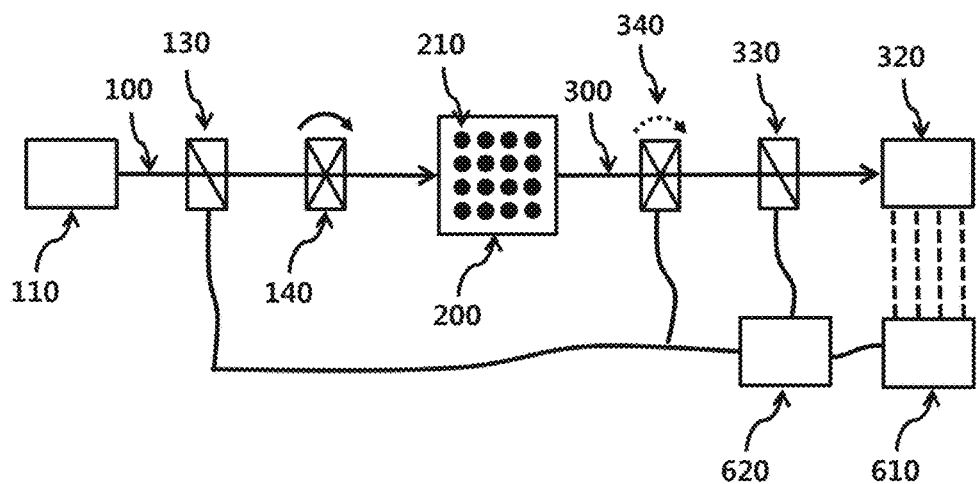
FIG. 14 is a schematic view of an optical element rotation type ellipsometer according to an eighth exemplary embodiment of the present invention.

In this case, when the second compensator 340 is selected as the scanning optical element as shown in FIG. 14, all of sixteen components of the Mueller-matrix for the sample may be obtained using the method of finding the solution of the simultaneous equations using Equations 6 to 14. However, when the polarizer 130 or the analyzer 330 is selected as the scanning optical element in FIG. 14, only twelve components, which are some of components of the Mueller-matrix for the sample may be obtained from the measurement. In the a single compensator rotation type Mueller-matrix ellipsometer of FIG. 14, when the first compensator 140 is selected as the constant velocity rotation optical element and the second compensator 340 is selected as the scanning optical element, Equation for the optical intensity measured by the photo-detector may be represented as follows:

$$I_{th}(C_1) = I_0(C_2) + \sum_{n=1}^{2} [A_{2n}(C_2)\cos(2nC_1) + B_{2n}(C_2)\sin(2nC_1)]. \quad (45)$$

Here, Fourier coefficients for an azimuth angle $C_1$ of the first compensator 140 may be represented by Fourier coefficients for an azimuth angle $C_8$ for an azimuth angle of the second compensator 340, which is the scanning optical element, as follows:

$$I_0(C_2) = d_0 + \sum_{r=1}^{2} [d_r\cos(2rC_2) + d_{2+r}\sin(2rC_2)], \quad (46)$$

$$A_{2n}(C_2) = A_{2n,0} + \sum_{r=1}^{2} [A_{2n,r}\cos(2rC_2) + A_{2n,2+r}\sin(2rC_2)]. \quad (47)$$

$$B_{2n}(C_2) = B_{2n,0} + \sum_{r=1}^{2} [B_{2n,r}\cos(2rC_2) + A_{2n,2+r}\sin(2rC_2)]. \quad (48)$$

Here, the Fourier coefficients for the azimuth angle for the scanning optical element are as follows:

$$d_0 = \quad (49)$$

$$2g_0 \left( \begin{array}{c} 2M_{11} + M_{31}\sin 2A(1 + \cos\delta_2) + \\ \cos(\delta_1/2)^2 \left\{ \begin{array}{c} \cos 2P[2M_{12} + M_{32}\sin 2A(1 + \cos\delta_2)] + \\ 2\sin 2P[M_{13} + M_{33}\sin A\cos A(1 + \cos\delta_2)] \end{array} \right\} + \\ \cos 2A(1 + \cos\delta_2)[M_{21} + \cos(\delta_1/2)^2(M_{22}\cos 2P + M_{23}\sin 2P)] \end{array} \right),$$

$$d_1 = 4g_0\sin 2A\sin\delta_2[M_{41} + \cos(\delta_1/2)^2(M_{42}\cos 2P + M_{43}\sin 2P)] \quad (50)$$

$$d_2 = -4g_0\cos 2A\sin\delta_2[M_{41} + \cos(\delta_1/2)^2(M_{42}\cos 2P + M_{43}\sin 2P)] \quad (51)$$

$$d_3 = 4g_0\sin(\delta_2/2)^2 \quad (52)$$

$$\left\{ \begin{array}{c} \cos 2A[M_{21} + \cos(\delta_1/2)^2(M_{22}\cos 2P + M_{23}\sin 2P)] \\ -\sin 2A[M_{31} + \cos(\delta_1/2)^2(M_{32}\cos 2P + M_{33}\sin 2P)] \end{array} \right\}$$

$$d_4 = 4g_0\sin(\delta_2/2)^2 \quad (53)$$

$$\left\{ \begin{array}{c} \sin 2A[M_{21} + \cos(\delta_1/2)^2(M_{22}\cos 2P + M_{23}\sin 2P)] \\ +\cos 2A[M_{31} + \cos(\delta_1/2)^2(M_{32}\cos 2P + M_{33}\sin 2P)] \end{array} \right\}$$

$$A_{2,0} = -2g_0\sin\delta_1\sin 2 \quad (54)$$
$$P[2M_{14} + M_{24}\cos 2A(1 + \cos\delta_2) + M_{34}\sin 2A(1 + \cos\delta_2)]$$

$$A_{2,1} = -4g_0M_{44}\sin\delta_1\sin\delta_2\sin 2P\sin 2A \quad (55)$$

$$A_{2,2} = -4g_0M_{44}\sin\delta_1\sin\delta_2\sin 2P\cos 2A \quad (56)$$

$$A_{2,3} = 4g_0\sin\delta_1\sin(\delta_2/2)^2\sin 2P(M_{34}\sin 2A - M_{24}\cos 2A) \quad (57)$$

$$A_{2,4} = -4g_0\sin\delta_1\sin(\delta_2/2)^2\sin 2P(M_{34}\cos 2A - M_{24}\sin 2A) \quad (58)$$

$$B_{2,0} = 2g_0\sin\delta_1\cos 2 \quad (59)$$
$$P[2M_{14} + M_{24}\cos 2A(1 + \cos\delta_2) + M_{34}\sin 2A(1 + \cos\delta_2)]$$

$$B_{2,1} = 4g_0M_{44}\sin\delta_1\sin\delta_2\cos 2P\sin 2A \quad (60)$$

$$B_{2,2} = -4g_0M_{44}\sin\delta_1\sin\delta_2\cos 2P\cos 2A \quad (61)$$

-continued $$B_{2,3} = 4g_0\sin\delta_1\sin(\delta_2/2)^2\cos 2P(M_{24}\cos 2A - M_{34}\sin 2A) \quad (62)$$

$$B_{2,4} = 4g_0\sin\delta_1\sin(\delta_2/2)^2\cos 2P(M_{34}\cos 2A - M_{24}\sin 2A) \quad (63)$$

$$A_{4,0} = 2g_0\sin^2\left(\frac{\delta_1}{2}\right) \quad (64)$$

$$\begin{bmatrix} \cos^2 P[2M_{12} + M_{22}\cos 2A(1+\cos\delta_2) + M_{32}\sin 2A(1+\cos\delta_2)] \\ -\sin^2 P[2M_{13} + M_{23}\cos^2 A(1+\cos\delta_2) + M_{33}\sin 2A(1+\cos\delta_2)] \\ -\sin^2 P[2M_{12} + M_{22}\cos 2A(1+\cos\delta_2) + M_{32}\sin 2A(1+\cos\delta_2)] \\ + M_{23}\sin^2 A\sin 2P(1+\cos\delta_2) \end{bmatrix}$$

$$A_{4,1} = -2g_0\sin 2A\sin\delta_2(\cos\delta_1 - 1)(M_{42}\cos 2P - M_{43}\sin 2P) \quad (65)$$

$$A_{4,2} = -2g_0\cos 2A\sin\delta_2(\cos\delta_1 - 1)(M_{42}\cos 2P - M_{43}\sin 2P) \quad (66)$$

$$A_{4,3} = -4g_0\sin^2\left(\frac{\delta_1}{2}\right)\sin^2\left(\frac{\delta_2}{2}\right)\begin{bmatrix} \cos 2A(M_{23}\sin 2P - M_{22}\cos 2P) \\ +\sin 2A(M_{32}\cos 2P - M_{33}\sin 2P) \end{bmatrix} \quad (67)$$

$$A_{4,4} = -4g_0\sin^2\left(\frac{\delta_1}{2}\right)\sin^2\left(\frac{\delta_2}{2}\right)\begin{bmatrix} \sin 2P(M_{33}\cos 2A + M_{23}\sin 2A) \\ -\cos 2P(M_{32}\cos 2A - M_{22}\sin 2A) \end{bmatrix} \quad (68)$$

$$B_{4,0} = 2g_0\sin^2\left(\frac{\delta_1}{2}\right) \quad (69)$$

$$\begin{bmatrix} \cos^2 P[2M_{13} + M_{23}\cos 2A(1+\cos\delta_2) + M_{33}\sin 2A(1+\cos\delta_2)] \\ +\sin 2P[2M_{12} - M_{22}\sin^2 A(1+\cos\delta_2)] \\ -\sin^2 P[2M_{13} + M_{23}\cos 2A(1+\cos\delta_2) + M_{33}\sin 2A(1+\cos\delta_2)] \\ +2\sin 2P\cos A\cos^2(\delta_2/2)(M_{32}\cos A + 2M_{32}\sin A) \end{bmatrix}$$

$$B_{4,1} = -2g_0\sin 2A\sin\delta_2(\cos\delta_1 - 1)(M_{43}\cos 2P + M_{42}\sin 2P) \quad (70)$$

$$B_{4,2} = 2g_0\cos 2A\sin\delta_2(\cos\delta_1 - 1)(M_{43}\cos 2P + M_{42}\sin 2P) \quad (71)$$

$$B_{4,3} = -4g_0\sin^2\left(\frac{\delta_1}{2}\right)\sin^2\left(\frac{\delta_2}{2}\right)\begin{bmatrix} \sin 2A(M_{33}\cos 2P + M_{32}\sin 2P) \\ -\cos 2A(M_{23}\cos 2P + M_{22}\sin 2P) \end{bmatrix} \quad (72)$$

$$B_{4,4} = -4g_0\sin^2\left(\frac{\delta_1}{2}\right)\sin^2\left(\frac{\delta_2}{2}\right)\begin{bmatrix} \sin 2A(M_{23}\cos 2P + M_{22}\sin 2P) \\ -\cos 2A(M_{33}\cos 2P + M_{32}\sin 2P) \end{bmatrix}. \quad (73)$$

A total of twenty five Fourier coefficients for the azimuth of the second compensator 340 are provided by linear Equations for sixteen components of the Mueller-matrix.

Therefore, when sixteen or more linear Equations among them are selected and a solution of simultaneous equations is found, all of the components of the Mueller-matrix may be obtained. One solution to the components of the Mueller-matrix obtained by this method is as follows:

$$M_{11} = \frac{1}{8g_0\sin^2(\delta_2/2)} \quad (74)$$

$$\begin{pmatrix} d_0 - d_4\sin 4A + \cot^2(\delta_1/2)\begin{bmatrix} \cos 4P(-A_{4,0} + A_{4,4}\sin 4A) \\ +\sin 4P(-B_{4,0} + B_{4,4}\sin 4A) \end{bmatrix} \\ -\cos 4A(1+\cos\delta_2)[d_3 - \cot^2(\delta_1/2)(A_{4,3}\cos 4P + B_{4,3}\sin 4P)] \\ +\cos\delta_2\begin{Bmatrix} -d_0 - d_4\sin 4A + \cot^2(\delta_1/2)[\cos 4P(A_{4,0} + A_{4,4}\sin 4A) \\ +(B_{4,0} + B_{4,4}\sin 4A)\sin 4P] \end{Bmatrix} \end{pmatrix}$$

$$M_{12} = \frac{1}{4g_0\sin^2(\delta_2/2)} \quad (75)$$

$$\begin{bmatrix} \cos 2P[A_{4,0} - \cot^2(\delta_2/2)(A_{4,3}\cos 4A + A_{4,4}\sin 4A)] \\ +\sin 2P[-A_{4,0} - \cot^2(\delta_2/2)(B_{4,3}\cos 4A + B_{4,4}\sin 4A)] \end{bmatrix}$$

$$M_{13} = \frac{1}{4g_0\sin^2(\delta_2/2)} \quad (76)$$

$$\begin{bmatrix} \cos 2P[B_{4,0} - \cot^2(\delta_2/2)(B_{4,3}\cos 4A + B_{4,4}\sin 4A)] \\ +\sin 2P[-A_{4,0} + \cot^2(\delta_2/2)(A_{4,3}\cos 4A + A_{4,4}\sin 4A)] \end{bmatrix}$$

$$M_{14} = \frac{1}{4g_0\sin^2(\delta_2/2)}[-A_{2,0} + \cot^2(\delta_2/2)(A_{2,3}\cos 4A + A_{2,4}\sin 4A)] \quad (77)$$

$$M_{21} = \quad (78)$$

$$\frac{1}{4g_0\sin^2(\delta_2/2)}\begin{bmatrix} \cos 2A[d_3 - \cot^2(\delta_1/2)(A_{4,3}\cos 4P + B_{4,3}\sin 4P)] \\ +\sin 2A[d_4 - \cot^2(\delta_1/2)(A_{4,4}\cos 4P + B_{4,4}\sin 4P)] \end{bmatrix}$$

$$M_{22} = \frac{1}{4g_0\sin^2(\delta_1/2)\sin^2(\delta_2/2)}\begin{bmatrix} \cos 2A(A_{4,3}\cos 2P + B_{4,3}\sin 2P) \\ +\sin 2A(A_{4,4}\cos 2P + B_{4,4}\sin 2P) \end{bmatrix} \quad (79)$$

$$M_{23} = \frac{1}{4g_0\sin^2(\delta_1/2)\sin^2(\delta_2/2)}\begin{bmatrix} \cos 2P(B_{4,3}\cos 2A + B_{4,4}\sin 2A) \\ -\sin 2P(A_{4,3}\cos 2A + A_{4,4}\sin 2A) \end{bmatrix} \quad (80)$$

$$M_{24} = \frac{A_{2,3}\cos 2A + A_{2,4}\sin 2A}{4g_0\sin\delta_1\sin^2(\delta_2/2)\sin 2P} \quad (81)$$

$$M_{31} = \quad (82)$$

$$\frac{1}{4g_0\sin^2(\delta_2/2)}\begin{bmatrix} \sin 2A[-d_3 + \cot^2(\delta_1/2)(A_{4,3}\cos 4P + B_{4,3}\sin 4P] \\ +\cos 2A[-d_4 - \cot^2(\delta_1/2)(A_{4,4}\cos 4P + B_{4,4}\sin 4P] \end{bmatrix}$$

$$M_{32} = \frac{1}{4g_0\sin^2(\delta_1/2)\sin^2(\delta_2/2)}\begin{bmatrix} -\sin 2A(A_{4,3}\cos 2P + B_{4,3}\sin 2P) \\ +\cos 2A(A_{4,4}\cos 2P + B_{4,4}\sin 2P) \end{bmatrix} \quad (83)$$

$$M_{33} = \frac{1}{4g_0\sin^2(\delta_1/2)\sin^2(\delta_2/2)}\begin{bmatrix} \sin 2A(-B_{4,3}\cos 2P + A_{4,3}\sin 2P) \\ +\cos 2A(A_{4,4}\cos 2P - A_{4,4}\sin 2P) \end{bmatrix} \quad (84)$$

$$M_{34} = \frac{-A_{2,4}\cos 2A + A_{2,3}\sin 2A}{4g_0\sin\delta_1\sin^2(\delta_2/2)\sin 2P} \quad (85)$$

$$M_{41} = \frac{d_1(\cos\delta_1 - 1) + 2\cos^2(\delta_1/2)(A_{4,1}\cos 4P + B_{4,1}\sin 4P)}{4g_0(\sin\delta_1 - 1)\sin\delta_2\sin 2A} \quad (86)$$

$$M_{42} = \frac{A_{4,1}\cos 2P + B_{4,1}\sin 2P}{4g_0\sin^2(\delta_1/2)\sin\delta_2\sin 2A} \quad (87)$$

$$M_{43} = \frac{B_{4,1}\cos 2P - A_{4,1}\sin 2P}{4g_0\sin^2(\delta_1/2)\sin\delta_2\sin 2A} \quad (88)$$

$$M_{44} = \frac{A_{2,1}}{4g_0\sin\delta_1\sin\delta_2\sin 2A\sin 2P}. \quad (89)$$

When the method as described above is applied to other exemplary embodiments, equations for the components of the Mueller-matrix for the sample may be obtained, respectively.

In the ellipsometer according to the present invention, a spectrometer, which is one among photo-detectors formed of a charge coupled device (CCD), a complementary metal oxide semiconductor (CMOS), a photodiode element, or the like, and including a plurality of pixels arranged in a linear structure or a two-dimensional plane structure, may be selected or a photo-detector formed of a photomultiplier tube (PMT), a photodiode, and the like, may be selected as the photo-detector. The photo-detector may include a cooling device selectively attached and used thereto in order to decrease a measurement error depending on a temperature.

The ellipsometer according to the present invention may include a remote light source shielding device that is disposed behind the light source on a movement path of the light and may shield the light irradiated from the light source to the sample by a remote control.

In the ellipsometer according to the present invention, the light source 110 may be a xenon lamp, a tungsten-halogen lamp, a deuterium lamp, a transfer of the light emitted from the lamp through an optical fiber, gas laser, a laser diode, or the like.

In the case of a semiconductor industry, since a size of a region to be measured in the sample is about several tens of micrometers, which is very small, a focus optical system allowing the incident light 100 to be focused on a local region of the sample 200 may be installed on a path in front of the sample 200, and a collimator again changing the light reflected or transmitted by the sample 200 into parallel light may be selectively included. Here, the focus optical system and the collimator may include one or more mirrors, include one or more lenses made of heterogeneous materials, or include an optical system including one or more mirrors and one or more lenses in order to correct chromatic aberration for a wide band wavelength, and may use the lenses or the mirrors coated with a single thin film or a multilayer thin film in order to improve transmission or reflection efficiency.

The ellipsometer according to the present invention may include a sample support for arranging the sample 200 and changing a measurement position, a 6 degree of freedom (DOF) system in which a 3 DOF parallel movement in a height direction and a width direction is possible, inclination adjustment having a 2 DOF is possible, and a rotation function is included, and a vacuum chuck for maintaining the sample in a stop state on the sample support at the time of the measurement.

The ellipsometer according to the present invention may include a sample arrangement system including laser emitting light for arranging the sample, an optical system allowing the light emitted from the laser to be incident to the sample in a specific direction, and a photo-detector collecting light reflected by the sample with respect to the incident light and detecting a position of the collected light, in order to arrange the sample for the measurement.

In order to decrease an error due to a change in a measurement environment, the ellipsometer according to the present invention may include an apparatus allowing a light path to be in an atmosphere state such as nitrogen gate, argon gas, or the like, for measurement for a wide band waveform, may be installed on a damping system in order to decrease an influence due to vibrations of a system and a measurement environment, and may include a constant temperature system for decreasing a measurement error due to a temperature change with respect to the light source, the optical elements, the sample, and the photo-detector.

Particularly, in the case of the semiconductor industry, or the like, it is important to measure a plurality of wafer samples within a rapid time. To thin end, the ellipsometer according to the present invention may include a sample storage container capable of storing the samples and a sample transporting apparatus sequentially taking out the samples one by one by the sample storage container and moving the samples to the sample support in order to measure physical properties of the samples, and again transporting the samples positioned on the sample support to the sample storage container when the measurement for designated points is completed.

It is preferable to obtain measurement data of the measured components of the Mueller-matrix, establish an optical theoretical equation for the sample, obtain data of the components of the Mueller-matrix calculated using a plurality of unknown parameters for a set region with respect to the established theoretical equation, and perform optimization with respect to the measurement data using a least squares algorithm from the data obtained by the calculation to obtain the physical property of the sample.

The ellipsometer according to the present invention may analyze various physical properties such as an interface property, a thickness of a thin film, a complex refractive index, a nano shape, an anisotropic property, a surface roughness, a composition ratio, crystallinity, and the like, of the sample from the measured Fourier coefficients and the measured components of the Mueller-matrix, and may be utilized in a measurement equipment for a semiconductor element process, a measurement equipment for a flat panel display process, a measurement equipment of a solar element, a thin film optical measurement equipment, a bio sensor, a gas sensor, or the like.

Particularly, in a physical property analyzing method that is very complicated, such as measurement of the shape of the nano pattern in a multi-channel spectroscopic ellipsometer according to the present invention, measurement data of the Fourier coefficients or the components of the Mueller-matrix for a sample to be measured are obtained, an optical theoretical equation for the sample is established, data of the Fourier coefficients or the components of the Mueller-matrix calculated using a plurality of unknown parameters determined in a set region are obtained with respect to the established theoretical equation, continuous functions for the unknown parameters are created with respect to the calculated data, and the continuous functions are optimized with respect to the measurement data using a least squares algorithm to obtain the physical property of the sample. In this case, the ellipsometer according to the present invention may include a large capacity high speed calculating system configured of a high performance parallel computer, rigorous coupled-wave analysis (RCWA) algorithm based analysis software, and a large capacity data storage in order to rapidly find the physical property of the sample from the measurement data of the Fourier coefficients or the components of the Mueller-matrix measured for the sample.

Figure 15:
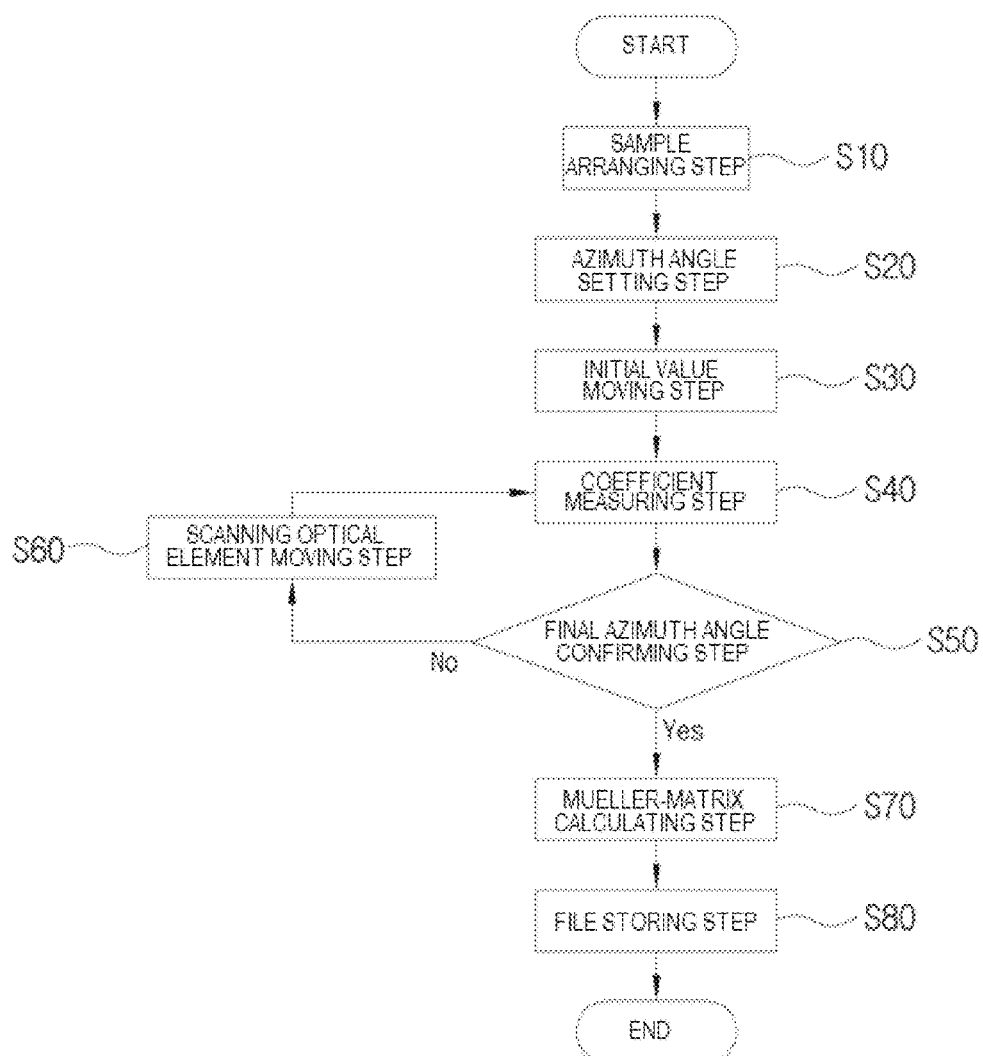
FIG. 15 is a flow chart showing a method for measuring a Mueller-matrix of a sample using the optical element rotation type ellipsometer according to the present invention.

A method for measuring a physical property of a sample using an optical element rotation type Mueller-matrix ellipsometer according to the present invention will be described with reference to FIG. 15.

The method for measuring a physical property of a sample using an optical element rotation type Mueller-matrix ellipsometer according to the present invention includes a sample arranging step S10, an azimuth angle setting step S20, an initial value moving step S30, a coefficient measuring step S40, a final azimuth angle confirming step S50, a scanning optical element moving step S60, a Mueller-matrix calculating step S70, and a file storing step S80.

The sample arranging step S10 is a step of mounting and arranging a sample of which a physical property is to be measured.

The azimuth angle setting step S20 is a step of setting azimuth angle values of a scanning optical element required in measurement.

The initial value moving step S30 is a step of moving an azimuth angle of the scanning optical element into an initial value by a program command in a computer.

The coefficient measuring step S40 is a step of measuring Fourier coefficients of a waveform of light intensity for a change in an azimuth angle of a constant velocity rotation optical element by a photo-detector.

The final azimuth angle confirming step S50 is a step of confirming whether the azimuth angle of the scanning optical element arrives at a final target point.

The final azimuth angle confirming step S50 proceeds to the Mueller-matrix calculating step S70 in the case in which the azimuth angle of the scanning optical element arrives at the final target point, and proceeds to the scanning optical element moving step S60 in the case in which the azimuth angle of the scanning optical element does not arrive at the final target point.

In the scanning optical element moving step S60, the scanning optical element moves to and stops at another designated azimuth angle position, and the method for measuring a physical property of a sample using an optical element rotation type ellipsometer according to the present invention proceeds to the coefficient measuring step S40, such that Fourier coefficients for the azimuth angle of the constant velocity rotation optical element are measured by the photo-detector.

The Mueller-matrix calculating step S70 is a step of calculating components of a Mueller-matrix for the sample by calculating Fourier coefficients for the azimuth angle of the scanning optical element when the azimuth angle of the scanning optical element arrives at the final target point.

The file storing step S80 is a step of storing the components of the Mueller-matrix calculated in the Mueller-matrix calculating step S70 as a file in the computer or outputting the components of the Mueller-matrix on a screen.

The invention claimed is:

1. An optical element rotation Mueller-matrix ellipsometer comprising:
   a light source emitting incident light toward a sample;
   a polarization modifying unit disposed between the light source and the sample on a movement path of the incident light, controlling a polarization state of the incident light emitted from the light source;
   a polarization analyzing unit receiving reflected light or transmitted light, analyzing a change in a polarization state of the reflected light or the transmitted light, the polarization state of the reflected light or the transmitted light being changed from that of the incident light polarized while passing through the polarization modifying unit due to reflection or transmission of the sample, wherein the polarization modifying unit or the polarization analyzing unit is mounted with a plurality of optical elements including a constant velocity rotation optical element rotating at a constant velocity and a scanning optical element;
   a photo-detector receiving the reflected light or the transmitted light passing through the polarization analyzing unit and measuring intensity of the received light as an electrical signal;
   a calculating device measuring and storing Fourier coefficient values of a waveform of light intensity depending on a change in an azimuth angle of the constant velocity rotation optical element by the photo-detector, calculating Fourier coefficient values for an azimuth angle of the scanning optical element from the measured Fourier coefficient values depending on the change in the azimuth angle of the constant velocity rotation optical element, and calculating components of a Mueller-matrix for the sample from the calculated Fourier coefficient values for the azimuth angle of the scanning optical element; and
   a computer controlling the azimuth angle of the scanning optical element, storing values of the components of the Mueller-matrix calculated from the calculating device as a file, and displaying the values of the components of the Mueller-matrix on a screen.

2. The optical element rotation Mueller-matrix ellipsometer of claim 1, wherein, when the waveform $[I(\theta_r, \theta_s)]$ of the light intensity measured by the photo-detector depending on the change in the azimuth angle of the constant velocity rotation optical element is as follows:

$$I(\theta_r, \theta_s) = I_0(\theta_s) + \sum_{n=1}^{N} [A_n(\theta_s)\cos(n\theta_r) + B_n(\theta_s)\sin(n\theta_r)],$$

{$\theta_r$: the azimuth angle of the constant velocity rotation optical element,
$\theta_s$: the azimuth angle of the scanning optical element,
$I_0(\theta_s)$: an average value of the light intensity or a zero order Fourier coefficient of the waveform of the light intensity depending on the change in the azimuth angle of the constant velocity rotation optical element,
$A_D(\theta_s)$ and $B_D(\theta_s)$: Fourier coefficients of the waveform of the light intensity depending on the change in the azimuth angle of the constant velocity rotation optical element, $$I_0(\theta_s) = d_0 + \sum_{r=1}^{R} [d_r\cos(2r\theta_s) + d_{R+r}\sin(2r\theta_s)].$$

$$A_n(\theta_s) = A_{n,0} + \sum_{r=1}^{R} [A_{n,r}\cos(2r\theta_s) + A_{n,R+r}\sin(2r\theta_s)].$$

$$B_n(\theta_s) = B_{n,0} + \sum_{r=1}^{R} [B_{n,r}\cos(2r\theta_s) + B_{n,R+r}\sin(2r\theta_s)].$$

$d_r$, $A_{D,r}$, $B_{D,r}$, ($r=0, 1, \ldots, 2R$): Fourier coefficients for the azimuth angle of the scanning optical element,
N: order number of highest order among Fourier coefficients of $A_D(\theta_s)$ and $B_D(\theta_s)$ that are not 0,
R: order number of highest order among Fourier coefficients of $d_r$, $A_{D,r}$, and $B_{D,r}$ that are not 0},
Fourier coefficients $[I_0(\theta_{s,i}), A_D(\theta_{s,i}), B_D(\theta_{s,i}); n=1, \ldots, N\, j=1, \ldots, j]$ of the waveform of the light intensity for the change in the azimuth angle of the constant velocity rotation optical element are measured by the calculating device in a state in which the azimuth angle of the scanning optical element of $2\pi$ are divided j times at a same interval and the scanning optical element moves to and stops at each azimuth angle position $[\theta_{s,i}=2\pi(j-1)/J, (j=1, \ldots, J)]$,
values of Fourier coefficients $d_r$, $A_{D,r}$, $B_{D,r}$; $n=1, \ldots N$, $r=0, 1, \ldots, 2R$) for the azimuth angle of the scanning optical element from measured values of the Fourier coefficients of the waveform of the light intensity for the change in the azimuth angle of the constant velocity rotation optical element are calculated by the calculating device using discrete Fourier transformer as follows:

$$d_0 = \frac{1}{J}\sum_{j=1}^{J} I_0(\theta_{s,j});$$

$$d_r = \frac{2}{J}\sum_{j=1}^{J} I_0(\theta_{s,j})\cos(2r\theta_{s,j});$$

$$d_{R+r} = \frac{2}{J}\sum_{j=1}^{J} I_0(\theta_{s,j})\sin(2r\theta_{s,j});$$

$$A_{n,0} = \frac{1}{J}\sum_{j=1}^{J} A_n(\theta_{s,j});$$

-continued $$A_{n,r} = \frac{2}{J}\sum_{j=1}^{J} A_n(\theta_{s,j})\cos(2r\theta_{s,j});$$

$$A_{n,R+r} = \frac{2}{J}\sum_{j=1}^{J} A_n(\theta_{s,j})\sin(2r\theta_{s,j});$$

$$B_{n,0} = \frac{1}{J}\sum_{j=1}^{J} B_n(\theta_{s,j});$$

$$B_{n,r} = \frac{2}{J}\sum_{j=1}^{J} B_n(\theta_{s,j})\cos(2r\theta_{s,j});$$

$$B_{n,R+r} = \frac{2}{J}\sum_{j=1}^{J} B_n(\theta_{s,j})\sin(2r\theta_{s,j});$$

and
the components of the Mueller-matrix for the sample are calculated by the calculating device from the calculated values of Fourier coefficients for the azimuth angle of the scanning optical element.

3. The optical element rotation Mueller-matrix ellipsometer of claim 1, wherein the polarization modifying unit is configured of one polarizer,
the polarization analyzing unit is configured of one analyzer, and
the polarizer and the analyzer are selected as the constant velocity rotation optical element and the scanning optical element, respectively, at a time of measurement.

4. The optical element rotation Mueller-matrix ellipsometer of claim 1, wherein the polarization modifying unit is configured of one polarizer,
the polarization analyzing unit is configured of one analyzer,
the optical element rotation Mueller-matrix ellipsometer further comprises a second polarizer disposed between the light source and the polarizer on an axis line of the incident light, and
the polarizer and one of the analyzer and the second polarizer are selected as the constant velocity rotation optical element and the scanning optical element, respectively, at a time of measurement.

5. The optical element rotation Mueller-matrix ellipsometer of claim 1, wherein the polarization modifying unit is configured of one polarizer,
the polarization analyzing unit is configured of one analyzer, and
the analyzer and the polarizer are selected as the constant velocity rotation optical element and the scanning optical element, respectively, at a time of measurement.

6. The optical element rotation Mueller-matrix ellipsometer of claim 1, wherein the polarization modifying unit is configured of one polarizer,
the polarization analyzing unit is configured of one analyzer,
the optical element rotation Mueller-matrix ellipsometer further comprises a second analyzer disposed between the analyzer and the photo-detector on an axis line of the reflected light or the transmitted light, and
the analyzer and one of the polarizer and the second analyzer are selected as the constant velocity rotation optical element and the scanning optical element, respectively, at a time of measurement.

7. The optical element rotation Mueller-matrix ellipsometer of claim 1, wherein the polarization modifying unit is configured of one polarizer and one compensator,
the polarization analyzing unit is configured of one analyzer,
the polarizer is disposed between the light source and the sample on an axis line of the incident light,
the compensator is disposed between the polarizer and the sample on the axis line of the incident light, and
the compensator and one of the polarizer and the analyzer are selected as the constant velocity rotation optical element and the scanning optical element, respectively, at a time of measurement.

8. The optical element rotation Mueller-matrix ellipsometer of claim 1, wherein the polarization modifying unit is configured of one polarizer,
the polarization analyzing unit is configured of one compensator and one analyzer,
the compensator is disposed between the sample and the photo-detector on an axis line of the reflected light or the transmitted light,
the analyzer is disposed between the compensator and the photo-detector on the axis line of the reflected light or the transmitted light, and
the compensator and one of the polarizer and the analyzer are selected as the constant velocity rotation optical element and the scanning optical element, respectively, at a time of measurement.

9. The optical element rotation Mueller-matrix ellipsometer of claim 1, wherein the polarization modifying unit is configured of one polarizer and a first compensator,
the polarization analyzing unit is configured of a second compensator and one analyzer,
the polarizer is disposed between the light source and the sample on an axis line of the incident light,
the first compensator is disposed between the polarizer and the sample on the axis line of the incident light,
the second compensator is disposed between the sample and the photo-detector on an axis line of the reflected light or the transmitted light,
the analyzer is disposed between the second compensator and the photo-detector on the axis line of the reflected light or the transmitted light, and
one of the first compensator and the second compensator is selected as the constant velocity rotation optical element and one of the remaining optical elements other than the constant velocity rotation optical element is selected as the scanning optical element, at the time of measurement.

10. The optical element rotation Mueller-matrix ellipsometer of claim 1, wherein the light source is selected among a xenon lamp, a tungsten-halogen lamp, and a deuterium lamp, a transfer of the light emitted from the lamp through an optical fiber, gas laser, and a laser diode.

11. The optical element rotation Mueller-matrix ellipsometer of claim 1, wherein a spectrometer, which is one among photo-detectors formed of a charge coupled device (CCD), a complementary metal oxide semiconductor (CMOS), or a photodiode element, and including a plurality of pixels arranged in a linear structure or a two-dimensional plane structure, is selected or a photo-detector formed of a photomultiplier tube (PMT) and a photodiode is selected as the photo-detector.

12. A method for measuring a physical property of a sample using an optical element rotation Mueller-matrix ellipsometer, comprising:

a sample arranging step of mounting and arranging the sample;

an azimuth angle setting step of setting azimuth angle values of a scanning optical element required in measurement;

an initial value moving step of moving an azimuth angle of the scanning optical element into an initial value by a program command in a computer;

a coefficient measuring step of measuring Fourier coefficients of a waveform of light intensity for a change in an azimuth angle of a constant velocity rotation optical element by a photo-detector;

a final azimuth angle confirming step of confirming whether the azimuth angle of the scanning optical element arrives at a final target point;

a scanning optical element moving step of moving and stopping the scanning optical element to and at another designated azimuth angle position and measuring Fourier coefficients for the azimuth angle of the constant velocity rotation optical element by the photo-detector, in the case in which the azimuth angle of the scanning optical element does not arrive at the final target point in the final azimuth angle confirming step;

a Mueller-matrix calculating step of calculating components of a Mueller-matrix for the sample by calculating Fourier coefficients for the azimuth angle of the scanning optical element in the case in which the azimuth angle of the scanning optical element arrives at the final target point in the final azimuth angle confirming step; and a file storing step of storing the components of the Mueller-matrix calculated in the Mueller-matrix calculating step as a file in the computer or outputting the components of the Mueller-matrix on a screen.

\* \* \* \* \*